US009446127B2

United States Patent
Shih et al.

(10) Patent No.: US 9,446,127 B2
(45) Date of Patent: Sep. 20, 2016

(54) COMPOSITIONS INCLUDING ANDROGEN RECEPTOR DEGRADATION (ARD) ENHANCERS AND METHODS OF PROPHYLACTIC OR THERAPEUTIC TREATMENT OF SKIN DISORDERS AND HAIR LOSS

(75) Inventors: Charles C. Y. Shih, Solana Beach, CA (US); Ching-Yuan Su, Del Mar, CA (US); Hui-Kang Wang, San Diego, CA (US); Qian Shi, Chapel Hill, NC (US)

(73) Assignee: AndroScience Corporation, San Diego, CA (US)

( * ) Notice: Subject to any disclaimer, the term of this patent is extended or adjusted under 35 U.S.C. 154(b) by 391 days.

(21) Appl. No.: 12/221,396

(22) Filed: Jul. 31, 2008

(65) Prior Publication Data
US 2009/0035362 A1    Feb. 5, 2009

Related U.S. Application Data

(60) Provisional application No. 60/962,880, filed on Jul. 31, 2007.

(51) Int. Cl.
| A61K 9/127 | (2006.01) |
| A61K 31/12 | (2006.01) |
| A61K 31/34 | (2006.01) |
| A61K 31/7048 | (2006.01) |
| A61K 38/16 | (2006.01) |
| A61K 45/06 | (2006.01) |
| A61K 31/265 | (2006.01) |

(52) U.S. Cl.
CPC ............. *A61K 45/06* (2013.01); *A61K 31/265* (2013.01)

(58) Field of Classification Search
CPC . A61K 31/265; A61K 2300/00; A61K 45/06
See application file for complete search history.

(56) References Cited

U.S. PATENT DOCUMENTS

| 4,806,683 A | 2/1989 | Miyata et al. |
| 5,334,481 A | 8/1994 | Merrem |
| 5,399,463 A | 3/1995 | Merrem |
| 5,496,556 A | 3/1996 | Johnson |
| 5,609,858 A | 3/1997 | Buck |
| 5,637,310 A | 6/1997 | Johnson |

(Continued)

FOREIGN PATENT DOCUMENTS

| CA | 2455547 | 1/2004 |
| CA | 2482002 | 10/2004 |

(Continued)

OTHER PUBLICATIONS

Lee et al., J Clin Endocrinol Metab, 88:4043-4054 (2003).
(Continued)

*Primary Examiner* — Savitha Rao
(74) *Attorney, Agent, or Firm* — David R Preston & Associates; David R Preston

(57) ABSTRACT

The present invention includes methods and compositions useful for treating and preventing skin disorders, hair loss and other skin disorders. The compositions include an ARD enhancer in combination with a second compound or composition. In some embodiments the second compound is at least one of a bactericide, an antibiotic, an anti-microbial peptide, Vitamin A, a Vitamin A derivative, a retinoid, an anti-inflammatory compound, and anti-androgen compounds.

4 Claims, 24 Drawing Sheets

5-Hydroxy-7-(4-hydroxy-3-methoxyphenyl)-4-
[3-(4-hydroxy-3-methoxyphenyl]-acryloyl]-hepta-
4,6-dienoic acid ethyl ester
(ASC-J15)

1,7-Bis-(3,4-dimethoxyphenyl)-5-hydroxy-
hepta-1,4,6-trien-3-one (dimethyl curcumin)
(ASCJ-9)

(56) References Cited

U.S. PATENT DOCUMENTS

| | | | |
|---|---|---|---|
| 5,733,886 A | 3/1998 | Baroody et al. | |
| 5,780,676 A * | 7/1998 | Boehm et al. | 562/490 |
| 5,883,124 A | 3/1999 | Samid | |
| 5,958,645 A | 9/1999 | Hirose et al. | |
| 6,218,369 B1 | 4/2001 | Bombardelli et al. | |
| 6,790,979 B2 | 9/2004 | Lee et al. | |
| 7,355,081 B2 | 4/2008 | Lee et al. | |
| 7,455,860 B2 | 11/2008 | Gokaraju et al. | 424/725 |
| 2003/0198990 A1 | 10/2003 | Chang | |
| 2003/0203933 A1 | 10/2003 | Lee et al. | |
| 2004/0037902 A1 | 2/2004 | Pandol et al. | 424/756 |
| 2005/0187255 A1 | 8/2005 | Lee et al. | |
| 2005/0209205 A1* | 9/2005 | Shih et al. | 514/171 |
| 2006/0040000 A1 | 2/2006 | Gokaraju et al. | 424/725 |
| 2006/0199768 A1 | 9/2006 | Singleton | |
| 2006/0258752 A1 | 11/2006 | Vander Jagt et al. | |
| 2006/0275516 A1 | 12/2006 | Ram et al. | |
| 2007/0204412 A1 | 9/2007 | Arkles | |
| 2008/0103213 A1 | 5/2008 | Kurzrock et al. | |

FOREIGN PATENT DOCUMENTS

| | | | | |
|---|---|---|---|---|
| EP | 0114003 A1 | 7/1984 | | |
| JP | 2000-258904 | 9/2006 | | |
| WO | WO97/16403 | 5/1997 | | |
| WO | WO 01/12130 A1 | 2/2001 | | A61K 6/00 |
| WO | WO03/011280 A1 | 7/2001 | | |
| WO | WO03/088927 A3 | 4/2002 | | |
| WO | WO2005/072462 A2 | 8/2005 | | |
| WO | WO2006/029040 A2 | 3/2006 | | |
| WO | WO 2006/044379 A2 | 4/2006 | | |
| WO | WO 2007/076162 A2 | 5/2007 | | |

OTHER PUBLICATIONS

Mostad et al., Acta Chemica Scandinavica, 38:479-484 (1984).
Pedersen et al., Liebigs Ann Chem., 1557-1569 (1985).
Miyamoto et al., J. Natl. Cancer Inst., 99(7):558-568 (2007).
Yang et al., Nature Medicine, 13(3):348-353 (2007).
Leibowitz et al., The Oncologist., 6:177-182 (2001).
Chung et al., Carcinogenesis, 22(8):1201-1206 (2001).
Foley et al., Current Opinion in Urology, 13:31-37 (2003).
Singh et al., Cancer Epidemiology Biomarkers & Prevention, 12:933-939 (2003).
Abdullah et al., Human Mol. Genetics, 7(3):379-384 (1998).
Ashcroft and Mills, J. Clin. Investigation, 110(5):615-624 (2002).
Bailey et al., Human Mol. Genetics, 11(5):515-523 (2002).
Chen et al., Nature Medicine, 10(1):33-39 (2004).
Heinlein and Chang, Endocrine Reviews, 25(2):276-308 (2004).
Lee and Chang, J. Clin. Endo. & Metabolism, 88(9):4043-4054 (2003).
Lin et al., The EMBO Journal, 21(15):4037-4048 (2002).
Neckers, Clinical Cancer Research, 8:962-966 (2002).
Ohtsu et al., J. Med. Chem., 45:5037-5042 (2002).
Ohtsu et al., Bioorganic and Medicinal Chem., 11:5083-5090 (2003).
Shih and Bollom, Cellular Immunology, 130:160-175 (1990).
Shih and Truitt, Science, 238:344-347 (1987).
Shih and Truitt, Transplantation Proceedings, XIX(1):2664-2667 (1987).
Solit et al., Clinical Cancer Research, 8:986-993 (2002).
Xing et al., Carcinogenesis, 22(3):409-414 (2001).
Ye et al., Skin Pharmacol., 10:288-297 (1997).
Zhu et al., Carcinogenesis, 22(9):1399-1403 (2001).
Barkhaus, http://www.emedicine.com/neuro/topic421.htm (Last visited Nov. 29, 2005).
Harper and Fulton, http://www.emedicine.com/derm/topic2.htm (Last visited Nov. 29, 2005).
Lin et al., Journal of Medicinal Chemistry (2006), 49(13), 3963-3972.
Pedersen et al., Liebigs Annalen der Chemie (1985), (8), 1557-1569.
Mostad et al., Chemistry and Biochemistry (1984), B38(6), 479-484.
Van Baar et al., Journal of Mass Spectrometry (1998), 33(4), 319-327.
Supurdjan et al., Majalah Farmasi Indonesia (2005), 16(2), 100-104.
International Search Report from PCT/US 96/17524.
International Search Report from PCT/US 08/09300.
Jan. 8, 2009 search results for U.S. Appl. No. 12/008,145.
Assay Depot, Acne Models, www.assaydepot.com/service/acne (obtained Aug. 6, 2015).
Avci et al., Animal models of skin disease for drug discovery, Expert Opin. Drug Discov., 8(3):331-355 (2013).
Franz et al., The Hamster Flank Organ Model: Is it Relevant to Man?, The Journal of Investigative Dermatology, 93(4):475-479 (1989).
Gomez et al., Effect of 13-cis-Retinoic Acid on the Hamster Flank Organ, The Journal of Investigative Dermatology, 74(6):392-397 (1980).
Lai et al., The role of androgen and androgen receptor in skin-related disorders, Arch. Dermatol. Res., 304:499-510 (2012).
Ye et al., Effects of Topical Antiandrogen and 5-Alpha-Reductase Inhibitors on Sebaceous Glands in Male Fuzzy Rats, Skin Pharmacol., 10:288-297 (1997).
Zouboulis, Acne and Sebaceous Gland Function, Clinics in Dermatology, 22:360-366 (2004).
Hsu et al., Postgrad Med., 123(3):153-61 (2011) (Abstract only).
Materials from Medscape, Clinical Review: Topical Retinoids, www.medscape.com (obtained Mar. 16, 2016).
Materials from Adult Acne Treatment Reviews, Oral Retinoids for Adult Acne, www.adultacnetreatmentreviews.com (obtained Mar. 16, 2016).
Materials from WebMD, Retinoids for Acne, www.webmd.com (obtained Mar. 16, 2016).
Materials from Acne Science, Oral Retinoid Drugs in Acne Treatment, www.acnescience.com (obtained Mar. 16, 2016).
Yang et al., Nature Medicine, 13(3):348-352 (2007).
Soh et al., Journal of Pharmaceutical and Biomedical Analysis, 88:117-122 (2014).
He et al., Cancer Research, 74(16):4420-4430 (2014).
Yamashita et al., Neoplasia, 14:74-83 (2012).
Huang et al., Hypertension, 63:1345-1353 (2014).
Shang et al., Mol. Cancer Ther., PMID: 26264279 (Aug. 11, 2015).

* cited by examiner

Figure 1
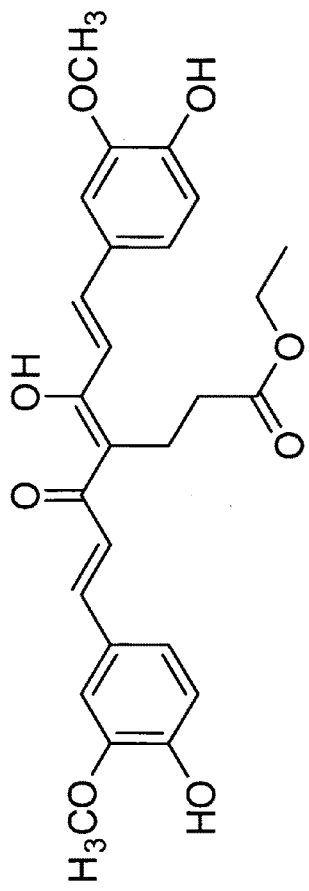
5-Hydroxy-7-(4-hydroxy-3-methoxyphenyl)-4-[3-(4-hydroxy-3-methoxyphenyl]-acryloyl]-hepta-4,6-dienoic acid ethyl ester
(ASC-J15)
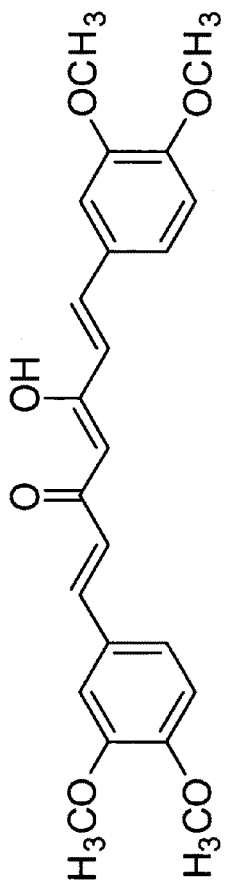
1,7-Bis-(3,4-dimethoxyphenyl)-5-hydroxy-hepta-1,4,6-trien-3-one (dimethyl curcumin)
(ASCJ-9)

Exemplary ARD Enhancers and Corresponding Anti-AR Activity
| Compound ID | Structure | Formula Molecular weight | *Anti-AR activity |
|---|---|---|---|
| ASC-Q9 | 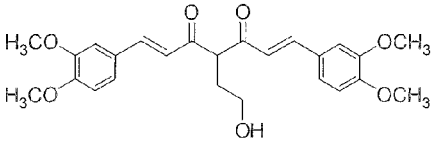 | $C_{25}H_{28}O_7$ 440.49 | ++ |
| ASC-Q44 | 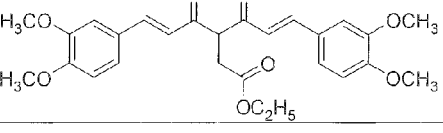 | $C_{27}H_{30}O_8$ 482.52 | ++ |
| ASC-Q49 | 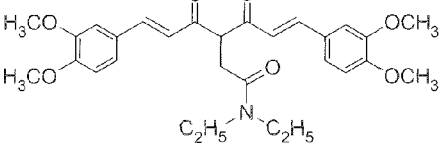 | $C_{29}H_{35}NO_7$ 509.59 | ++++ |
| ASC-Q77 | 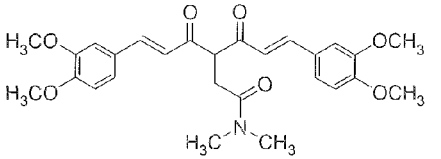 | $C_{27}H_{31}NO_7$ 481.54 | +++ |
| ASC-Q98 | 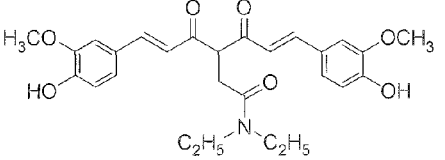 | $C_{27}H_{31}NO_7$ 481.54 | +++ |
Figure 2A

| | | | |
|---|---|---|---|
| ASC-Q99 | (structure) | C$_{26}$H$_{28}$O$_7$ 452.50 | ++ |
| ASC-Q101 | (structure) | C$_{26}$H$_{28}$O$_6$ 436.50 | ++ |
| ASC-Q102 | (structure) | C$_{25}$H$_{28}$O$_6$ 424.49 | +++ |
| ASC-Q103 | (structure) | C$_{27}$H$_{32}$O$_6$ 452.54 | +++ |
| ASC-Q110 | (structure) | C$_{25}$H$_{26}$O$_6$ 422.47 | ++ |
| ASC-Q111 | (structure) | C$_{27}$H$_{28}$O$_6$ 448.51 | ++ |
| ASC-Q113 | (structure) | C$_{28}$H$_{30}$O$_7$ 478.53 | +++ |

Figure 2B

| | | | |
|---|---|---|---|
| ASC-Q116 | | C$_{31}$H$_{28}$O$_6$ 496.55 | ++ |
| ASC-JM1 | | C$_{32}$H$_{32}$O$_6$ 512.59 | +++ |
| ASC-JM2 | | C$_{25}$H$_{27}$NO$_7$ 453.48 | ++ |
| ASC-JM4 | | C$_{34}$H$_{34}$O$_9$ 586.63 | +++++ |
| ASC-JM5 | | C$_{47}$H$_{48}$O$_{12}$ 804.87 | ++++ |
| ASC-JM6 | | C$_{26}$H$_{26}$O$_8$ 466.48 | ++ |

Figure 2C

| | | | |
|---|---|---|---|
| ASC-JM7 | (structure) | C$_{32}$H$_{32}$O$_8$ 544.59 | ++++- |
| ASC-JM12 | (structure) | C$_{27}$H$_{30}$O$_6$ 450.52 | ++++ |
| ASC-JM13 | (structure) | C$_{30}$H$_{36}$O$_6$ 492.60 | ++ |
| ASC-JM14 | (structure) | C$_{26}$H$_{27}$F$_3$O$_6$ 492.48 | ++++ |
| ASC-JM16 | (structure) | C$_{26}$H$_{28}$O$_6$ 436.50 | ++ |
| ASC-JM17 | (structure) | C$_{28}$H$_{32}$O$_6$ 464.55 | ++++ |

Figure 2D

| ASC-JM18 | ![structure] | C$_{25}$H$_{26}$O$_6$ 422.47 | ++ |
| ASC-JM19 | ![structure] | C$_{24}$H$_{23}$F$_3$O$_6$ 464.43 | +++ |

*Note:
Anti-AR activity was assayed in human prostate cancer cell line (LNCaP), by measuring the reduction of AR protein using Western Blot analysis. The relative potency of compounds is expressed as % AR protein reduction, in compare to the vehicle control, after cells were incubated with compound for 48 hours.

Figure 2E

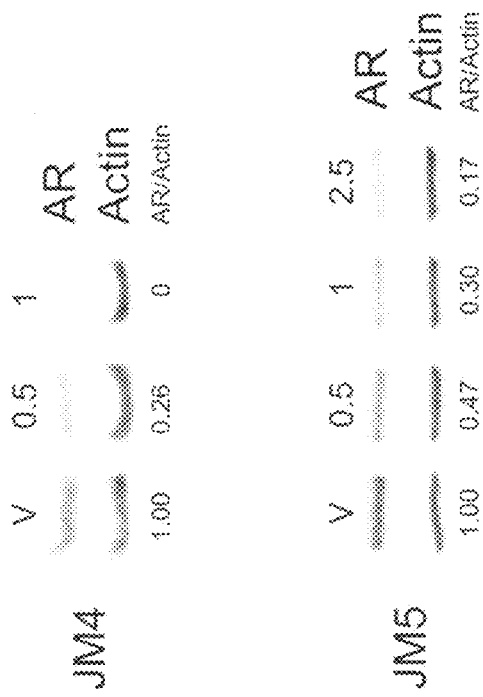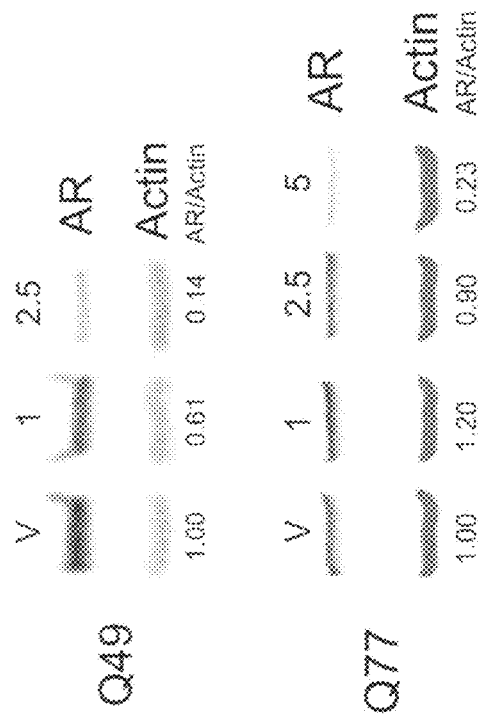
Figure 3B

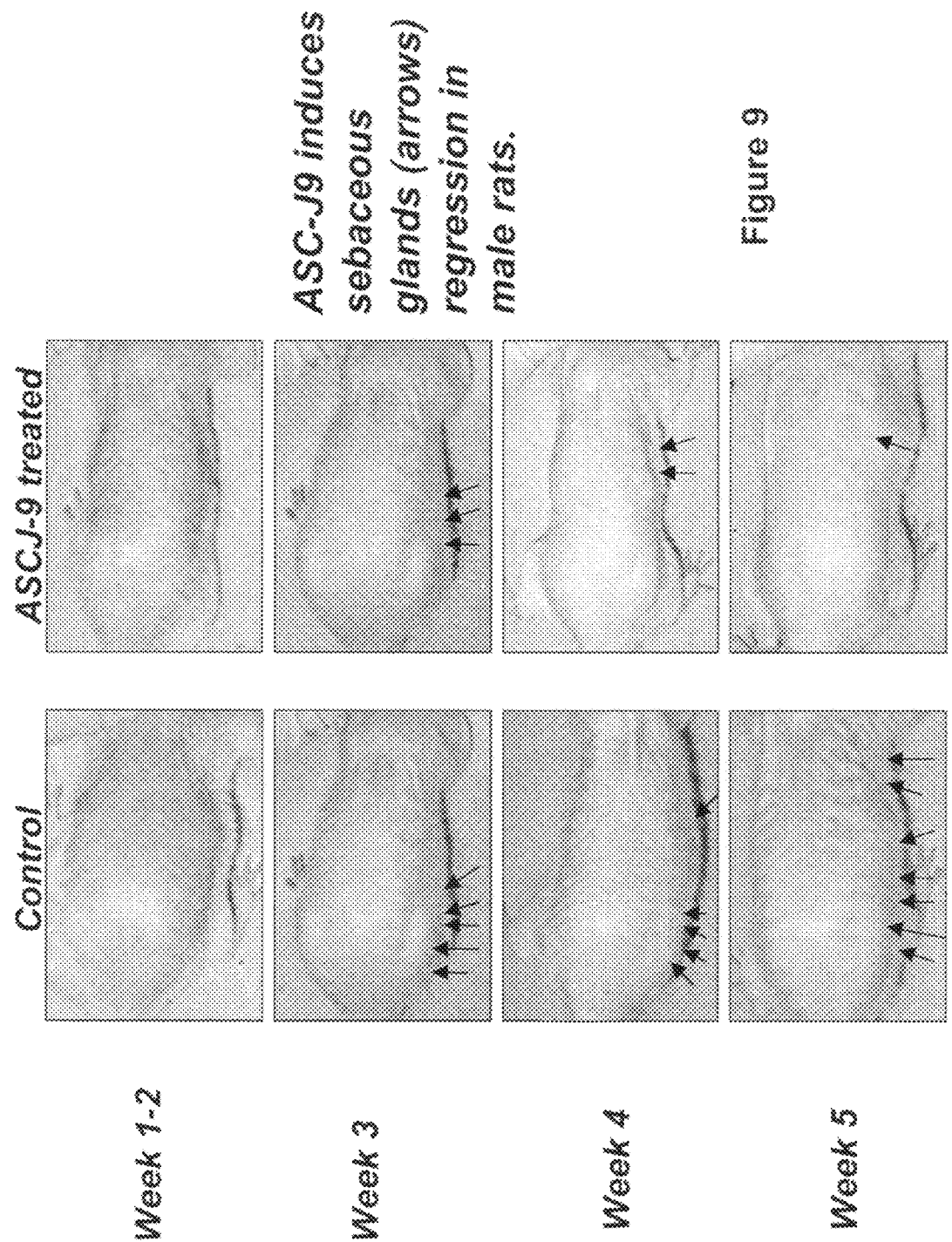
Figure 9. ASC-J9 induces sebaceous glands (arrows) regression in male rats.

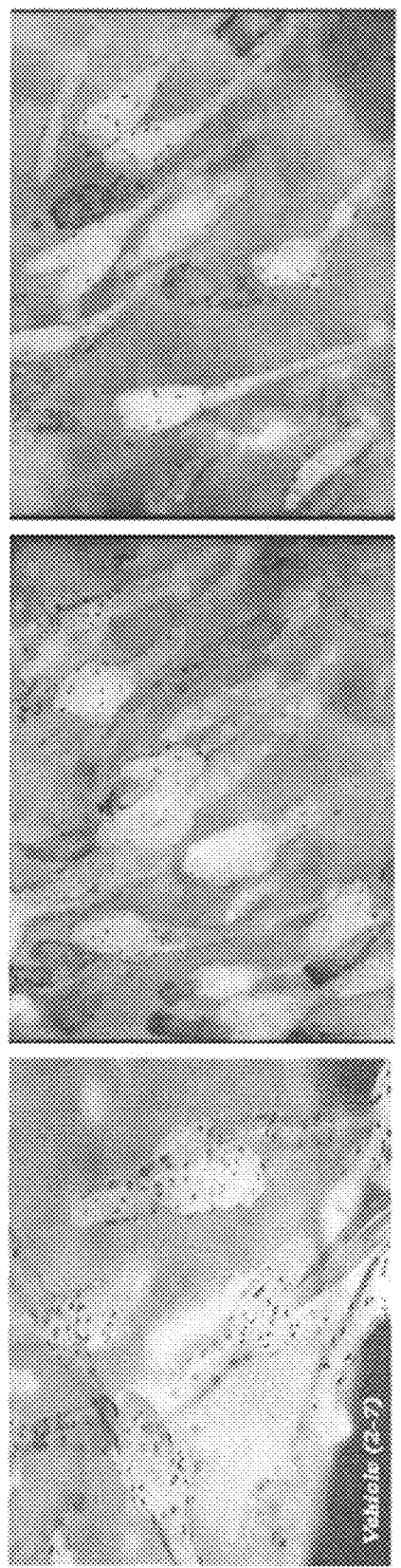
Figure 10A-C

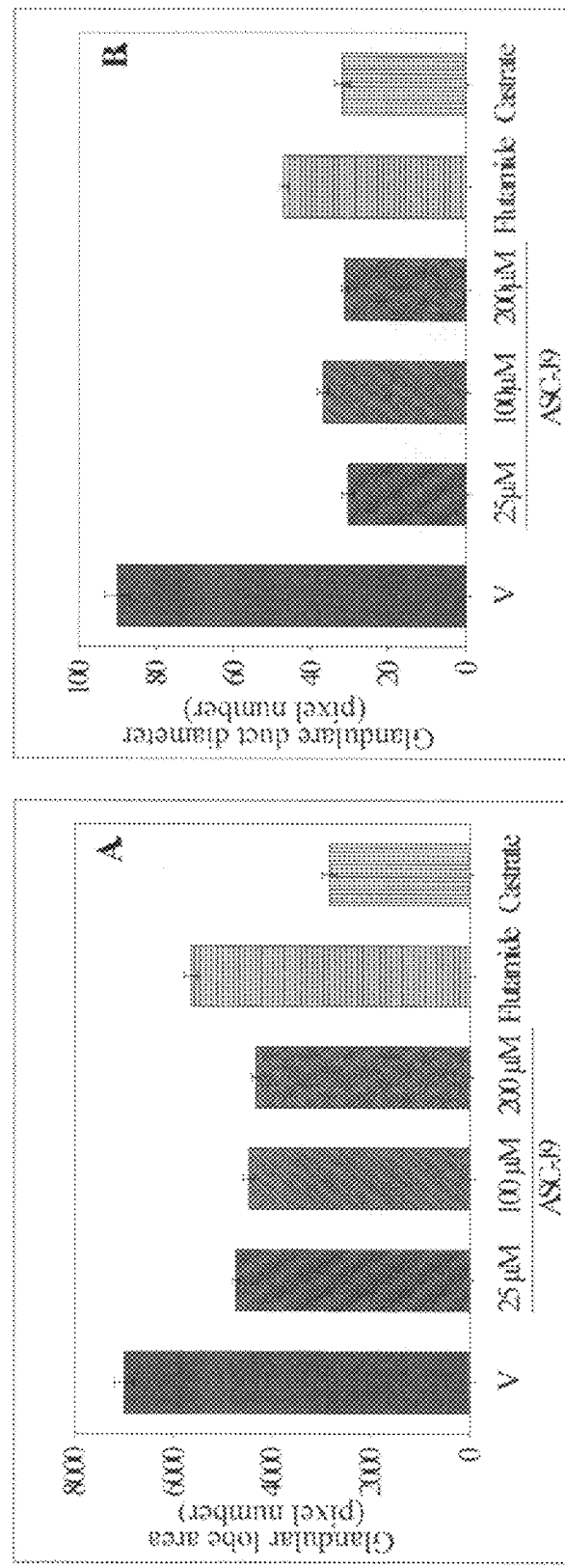
Figure 10D-E

*ASC-J9 overcomes testosterone-induced hair growth suppression (2 right mice), in a depilation model*

*ASCJ-9 inhibits human prostate cancer (LNCaP) growth in nude mice*

Animals received ASCJ-9 ip injection (100 mg/kg, 3 times per week) for 7 Weeks, their tumor weight reduced 75% and serum PSA level reduced 90% as compare to the vehicle control animal

COMPOSITIONS INCLUDING ANDROGEN RECEPTOR DEGRADATION (ARD) ENHANCERS AND METHODS OF PROPHYLACTIC OR THERAPEUTIC TREATMENT OF SKIN DISORDERS AND HAIR LOSS

CROSS REFERENCE TO RELATED APPLICATIONS

The present invention claims benefit of priority to U.S. patent application Ser. No. 60/962,880, filed on Jul. 31, 2007, the entire contents of which are incorporated herein by reference in its entirety.

TECHNICAL FIELD

The present invention relates generally to methods and compositions useful for the treatment and prevention of skin disorders and hair loss, and more specifically to methods and compositions including an Androgen Receptor Degradation (ARD) enhancer provided in combination with a second compound or composition; the combination having beneficial activity or effects against skin disorders or hair loss.

BACKGROUND

Reduced self-esteem and depression is often present among those suffering from skin disorders and hair loss. In some instances psychological effects can be dramatic. Thus, the development of therapeutics to treat each medical condition is underway. The present invention addresses current therapies and provides new compositions that have promising results.

Acne (acne vulgaris) is a common inflammatory disease of the skin, caused by changes in the pilosebaceous units (skin structures including a hair follicle and its associated sebaceous gland) in response to sexual hormones. Acne is most often found on the face, chest and back. The condition is most common at puberty and generally tends to disappear, or decrease when the individual reaches the early twenties. However, acne can remain problematic into the third to fifth decade of life and in some instances even longer.

The basic acne lesion, called a comedo or comedone is an enlarged hair follicle plugged by excess oil secreted from the sebaceous gland in response to androgen. In addition, dead skin cells and the build up of the bacteria *Propionibacterium acnes* also contribute to enlarging hair follicles. *P. acnes* produce lipases which can split triglycerides into free fatty acids, which can irritate the follicular cells. The severity of acne can range from mild to severe. In addition to comedones, papules, pustules, nodules and inflammatory cysts are also lesions associated with acne. Non-inflamed sebaceous cysts, also called epidermoid cysts, may occur in association with inflammatory acne or alone but are not usually a constant feature. After resolution of acne, unsightly scars may remain.

Many products are available for the treatment of acne, the most popular including exfoliation products, antibiotics, topical bactericides, retinoids, and oral hormonal treatments. However each has potential drawbacks. More recently compounds capable of inducing degradation of the androgen receptor are under investigation as potential treatment for androgen receptor associated disorders.

Exfoliation either manually or chemically attempts to remove dead skins cells from the skin therefore reducing the likelihood of blocked pores. Exfoliation may be performed manually by using scrubbing products or may be performed chemically. The chemical exfoliation products salicylic acid and glycolic acid are available as a chemical peel. Exfoliation may result in flaking of the skin or irritation.

Antibiotics, either oral or topical, are commonly used to attack the bacteria *P. acnes*. Erythromycin, clindamycin, cotrimoxazole and numerous tetracycline derivatives (such as doxycycline, oxytetracycline, tetracycline chloride, limecyline and minocyline) are commonly prescribed as treatments for acne. Although antibiotics are effective at reducing bacterial colonies, reducing the presence of bacteria does not affect the oil secretion from the sebaceous gland, and the potential development of bacterial strains resistant to antibiotics is also a concern.

Like antibiotics, topical bactericides such as benzoyl peroxide attack bacteria *Propionibacterium acnes*. Although topical bactericides have the added benefit over antibiotics in that bacterial resistance is not found, the powerful oxidizer benzoyl peroxide can cause skin dryness, redness and can bleach clothing. Therefore methods to reduce the frequency of use or decreased concentrations of the powerful oxidizer would be a significant benefit over current therapies.

Retinoids such as the topical retinoids tretinoin (brand name Retin-A), adapalene (brand name Differin) and tazarotene (brand name Tazorac) are related to vitamin A and may regulate the cell cycle in the follicle lining. Topical retinoids can cause significant irritation of the skin. Oral retinoids such as the vitamin A derivative isotrenoin (brand name Accutane and Sotret) are believed to reduce oil secretion from the sebaceous gland but are also believed to have adverse side effects.

Androgenetic Alopecia is the most common form of hair loss in men. This condition is also commonly known as male-pattern baldness. Hair is lost in a well-defined pattern, beginning above both temples. Over time, the hairline recedes to form a characteristic "M" shape. Hair also thins at the crown of the head, often progressing to partial or complete baldness. The pattern of hair loss in women differs from male-pattern baldness. In women, the hair becomes thinner all over the head, and the hairline does not recede. Androgenic alopecia in women rarely leads to total baldness. Minoxidil is the only FDA-approved treatment for androgenetic alopecia; however, it is not targeted at the function of androgen and effectiveness is not widespread.

Higher serum androgen levels have been correlated with the presence of acne, androgenetic alopecia and hair loss in some women. Androgens are known for their effects on sebum excretion, and terminal sebocyte differentiation is assisted by peroxisome proliferator-activated receptor ligands. Hormonal treatments have been identified as having a potential effect on acne and androgenetic alopecia. Compounds with anti-androgenic properties include estrogens combined with progestins, such as ethinyl estradiol with cyproterone acetate, chlormadinone acetate, desogestrel, drospirenone, levonogestrel, norethindrone acetate, norgestiate. Other compounds used as anti-androgens include those that directly blocking the androgen receptor (such as flutamide) or inhibit androgen activity at various levels such as corticosteroids, spironolactone, cimetidine and ketoconazole. However androgens are involved in many biological processes; therefore, blocking or inhibiting androgen binding to its corresponding receptor results in increased levels of available androgen in the surrounding environment, which affects other androgen associated biological processes and can lead to undesirable side effects.

A new group of anti-androgenic compounds have been proposed that induce degradation of the androgen receptor. These compounds differ from conventional anti-androgens that block androgen receptor and ligand (androgen) binding. Unlike widely used anti-androgen therapies, these new compounds prevent the accumulation of excess ligands (androgen) to act on androgen receptor and thus are predicted to have fewer adverse effects. Although a variety of compounds are proposed, the technology is not yet clinically available and the long term effects are not yet known.

Although the majority of treatments for skin disorders utilize a single active compound or pharmaceutical, a combination of therapies including a topical retinoid combined with oral antibiotics has been explored in mild to moderate inflammatory acne. These combinations are believed to lead to a rapid dose reduction and quicker discontinuation of oral antibiotics increasing the effectiveness and reducing the development of bacterial resistance to antibiotics. Although combinations of therapies have been proposed, current therapies attempt to reduce symptoms associated with skin disorders and do not selectively target the cause of the disorder. Therefore there remains a need to develop methods and compositions that selectively target pathways that lead to the skin disorders while also treating associated symptoms.

SUMMARY

The present invention addresses deficiencies in current treatments of skin disorders and hair loss and provides related benefits. Currently there are no androgen-associated topical therapies that attempt to block androgen activity and the only oral treatment for androgenetic aplopecia, finasteride, is used to block the conversion of testosterone into DHT; there is no method to modulate the presence or availability of the underlying androgen receptor and thus do not target the cause of the disorder. The present invention addresses this deficiency by providing compositions and methods that at least in part modulate the presence of the androgen receptor itself and thus provides a more effective treatment. In some embodiments, a combined modulation approach is provided, wherein at least one compound is an ARD enhancer as described herein.

The methods and compositions of the present invention treat or prevent a variety of skin disorders and hair disorders by administering one or more of the disclosed compounds or derivatives thereof. The ARD enhancers included herein include but are not limited to those provided in FIGS. 1 and 2. Among the ARD enhancers include ASC-J9, ASC-J15, ASC-Q9, ASC-Q44, ASC-Q49, ASC-Q77, ASC-Q98, ASC-Q99, ASC-Q101, ASC-Q102, ASC-Q103, ASC-Q110 or ASC-Q111, ASC-Q113, ASC-Q116, ASC-JM1, ASC-JM2, ASC-JM4, ASC-JM5, ASC-JM6, ASC-JM7, ASC-JM12, ASC-JM13, ASC-JM14, ASC-JM16, ASC-JM17, ASC-JM18 and ASC-JM19.

In one aspect of the present invention compositions for the prevention or treatment of a skin disorder is provided. In this aspect, the first compound is an androgen receptor degradation (ARD) enhancer. ARD enhancers are compounds that modulate the degradation of the androgen receptor, which is different from conventional anti-androgens that interfere the receptor-ligand (androgen) binding. In one embodiment, the ARD enhancer induces degradation of the androgen receptor. In another embodiment, the ARD enhancer increases the rate of androgen receptor degradation compared to the absence of an ARD enhancer. In yet another embodiment, the ARD enhancer prevents the aggregation of mutant androgen receptors. In still another embodiment, an ARD enhancer prevents androgen and androgen receptor (a transcription factor)-mediated gene activation. The second compound is selected from at least one of variety of compounds including a bactericide, an antibiotic, an anti-microbial peptide, Vitamin A, a Vitamin A derivative, or a retinoid, and an inflammatory compound. The combination of such compounds will provide more effective treatments for skin disorders while reducing adverse effects in comparison to current treatments. Though nonlimiting the inventors believe the ARD enhancer decrease oil secretion from a sebaceous gland, reduce proliferation of sebocytes or inhibit or reducing sebocyte differentiation. The inventors believe the second compound may target bacteria colonies or will provide additional anti-inflammatory assistance as needed when treating a variety of skin disorders. Thus, the present invention allows for the treatment of symptoms as well as modulation of a pathway to prevent or limit the occurrence of the skin disorders.

In another aspect of the present invention a pharmaceutical composition is disclosed, the pharmaceutical composition including an androgen receptor degradation (ARD) enhancer, a bactericide and a pharmaceutically acceptable carrier. The pharmaceutical may be topically applied, injected and the like depending on the desired route of administration. In the preferred embodiment the bactericide is benzoyl peroxide.

In yet aspect of the present invention a pharmaceutical composition is disclosed, the pharmaceutical composition including an androgen receptor degradation (ARD) enhancer, an antibiotic and a pharmaceutically acceptable carrier.

In still another aspect of the present invention a pharmaceutical composition is disclosed, the pharmaceutical composition including an androgen receptor degradation (ARD) enhancer, an anti-microbial peptide, and a pharmaceutically acceptable carrier.

In still another aspect of the present invention a pharmaceutical composition is disclosed, the pharmaceutical composition including an androgen receptor degradation (ARD) enhancer, Vitamin A, a Vitamin A derivative or a retinoid, and a pharmaceutically acceptable carrier.

In still another aspect of the present invention a pharmaceutical composition is disclosed, the pharmaceutical composition including an androgen receptor degradation (ARD) enhancer, an anti-inflammatory compound, and a pharmaceutically acceptable carrier.

In still another aspect of the present invention a method of treating or preventing a skin disorder is provided including administering to an individual in need thereof a therapeutically effective amount of a pharmaceutical composition of the present invention. In one embodiment the pharmaceutical composition includes an ARD enhancer and a bactericide. In another embodiment the pharmaceutical composition includes an ARD enhancer and an antibiotic. In yet another embodiment the pharmaceutical composition includes an ARD enhancer and an anti-microbial peptide. In still another embodiment the pharmaceutical composition includes and ARD enhancer and Vitamin A, a Vitamin A derivative or a retinoid. In still another embodiment the pharmaceutical composition includes an ARD enhancer and an anti-inflammatory compound. In various embodiments, nonlimiting examples of skin disorders are acne, alopecia, atopic dermatitis, rosacea, lupus, axillary osmidrosis, a wound and the like.

In still other aspects of the present invention, the combinations of compounds are provided as a cosmetic in a cosmetic formulation. The invention including a cosmetic composition including, in a cosmetically acceptable carrier, an ARD enhancer and a compound such as but not limited to a bactericide, an antibiotic, an anti-microbial peptide, Vitamin A, a Vitamin A derivative or a retinoid, and an anti-inflammatory compound.

In still other aspects of the present invention an ARD enhancer is combined with at least one composition or compound for the treatment or prevention of hair loss. The ARD enhancer may be combined with oligopeptides, peptides, extracts, nucleotides and the like. In some embodiments, the compositions of the present invention treat androgenetic alopecia. In some embodiments, a compound suspected of preventing hair loss is provided in combination with a compound suspected of stimulating hair growth.

BRIEF DESCRIPTION OF THE DRAWINGS

FIG. 1 depicts a structural formula of ASC-J15 and ASC-J9, exemplary ARD enhancers.

FIGS. 2A, 2B, 2C, 2D, and 2E depict a table of structural formulas of various ARD enhancers with corresponding values for relative potency (corresponding to percent AR reduction, compared to vehicle control). Anti-AR activity was assayed by western blot analysis after 48 hours of incubation of the human prostate cancer cell line LNCaP in the presence of the corresponding ARD enhancer. The value indications for activity can be found in Table 1 provided within Example 2.

FIGS. 3A and 3B depict western blot analysis demonstrating the reduction of Androgen Receptor (AR) protein expression in human prostate cancer cells (LNCaP) after exposure to compounds (3A) ASC-Q49, ASC-Q103, ASC-JM12, ASC-JM14; and (3B) ASC-Q49, ASC-Q77, ASC-JM4, and ASC-JM5.

Referring to FIG. 4A, the results demonstrate that while DHT promote LNCaP cell growth in culture, ASC-J9 significantly inhibits cell growth regardless in the presence or absence of DHT. FIG. 4B depicts normalized androgen receptor signals for the ASC-J9 sample as a percentage of baseline (Day 0) value. Cell lysates collected from cell cultured with ASC-J9 (FIG. 4A) and AR expression was detected by Western Blot. Data indicated that the inhibition of AR expression in LNCaP cells, induced by ASC-J-9, is in correlation with cell growth inhibition.

FIG. 9 depicts representative photographs of Fuzzy rats treated as described in detail in Example 6. Fuzzy rats were treated with topical creams containing vehicle only (left side animal) or ASC-J9 (25 micromolar, right side animal) for the times indicated. The photographs show that bands of sebaceous glands and sebum secretion (skin color) were reduced within 4-5 weeks in the Fuzzy rats treated with ASC-J9 (right side animal).

FIG. 10 depicts representative photographs (FIGS. 10A-C) and graphical representations of duct and lobe size (FIGS. 10D, 10E) of sebaceous glands in Fuzzy rat skin. Skin tissue samples (split skin) were prepared and examined by microscopy. FIG. 10A-C are photographs depicting the duct and lobe of the sebaceous gland (of a split skin sample) upon treatment with a vehicle control (8A) or compound ASC-J9 (8B) and a castrated animal (8C). In FIG. 10D, size of glandular lobes were measured by tracing the edges of the well-preserved glandular lobules, and then quantified with Image J software, and expressed as pixel counts contained within the traced areas. The data obtained showed topical treatment with the vehicle only (control cream) did not produce a significant change in glandular lobe size. Topical treatment of male rats with the various concentration of test compounds ASC-J9 resulted in a significant reduction in the size of the sebaceous glandular lobe, though not to the extent caused by castration, but are better than the conventional anti-androgen flutamide. FIG. 10E depicts representative data showing that ASC-J9 applied to skin significantly reduced the size of ducts of sebaceous glands in male Fuzzy rats comparable to the castration effect and better than flutamide.

DETAILED DESCRIPTION OF THE INVENTION

Figure 3A:
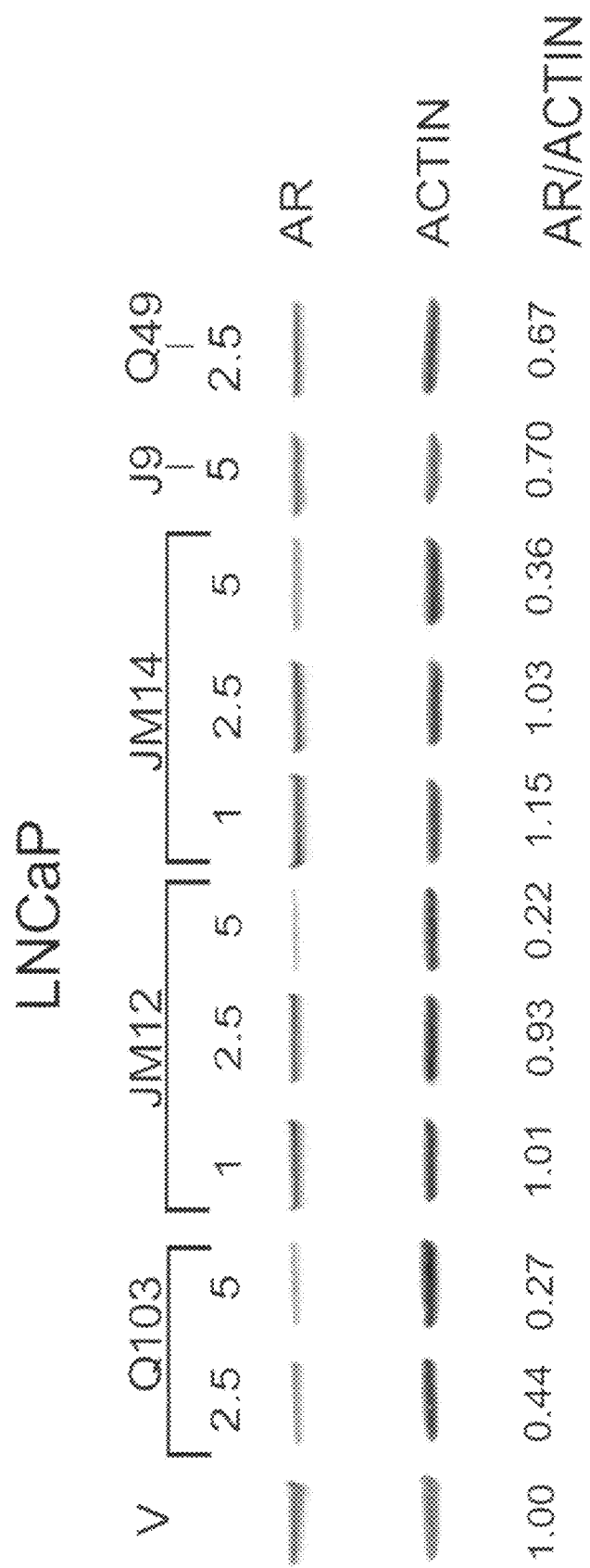

The present invention incorporates by reference U.S. patent application Ser. No. 12/008,124 entitled, "Compounds with (substituted phenyl)-propenal moiety, their derivatives, biological activity, and uses thereof." Methods of synthesis and thus methods of preparation of ARD enhancers described herein may be found the cited application. Further definitions may also be found in the incorporated application.

A. Definitions

Unless defined otherwise, all technical and scientific terms used herein have the same meaning as is commonly understood by one of ordinary skill in the art to which this invention belongs. All patents, applications, published applications and other publications are incorporated by reference in their entirety. In the event that there are a plurality of definitions for a term herein, those in this section prevail unless stated otherwise.

The term "androgen receptor" as used herein or "AR" refers to the intracellular protein receptor that specifically binds androgens, testosterone and DHT. AR includes all mammalian isoforms, splice variants, mutants and polymorphisms of the androgen receptor.

The term "cosmetically acceptable" as used herein refers to approved or approvable by a regulatory agency of the Federal or a state government as a cosmetic for use in animals, and more particularly in humans. The term "cosmetically acceptable carrier" as used herein refers to an approved or approvable diluent, adjuvant, excipient or carrier, such as but not limited to a liposome, with which a compound is incorporated or administered.

The term "enhancing degradation of the androgen receptor" as used herein refers to reducing the quantity of androgen receptors or increasing the rate of degradation (reduction) of the androgen receptors when compared to a placebo or no treatment.

The term "extended release" as used herein refers to dosage form that provides for the delayed, slowed over a period of time, continuous, discontinuous, or sustained release of a compound or composition.

The term "peptide" as used herein refers to a series of amino acids linked together. An "oligopeptide" refers to a peptide that is short in length.

The term "pharmaceutically acceptable" as used herein refers to approved or approvable by a regulatory agency of the Federal or a state government for use in animals, and more particularly in humans. The term "pharmaceutically acceptable carrier" refers to an approved or approvable diluent, adjuvant, excipient or carrier, such as but not limited to a liposome, with which a compound is incorporated or administered.

The term "prodrug" as used herein refers to a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug.

The term "therapeutically effective amount" as used herein refers to the amount of a compound or composition that, when administered to a patient for treating a disease or disorder, is sufficient to affect such treatment for the disease or disorder. The "therapeutically effective amount" will vary depending on the compound or composition, the disease or disorder and its severity and the age and weight of the patient to be treated.

B. Compositions for the Treatment of Skin Disorders

It's the belief of the inventors that the combinations of compounds provided herein will have increased therapeutic utility when compared to current therapies for the treatment of skin disorders. Thus, in one aspect of the present invention, a composition for the prevention or treatment of a skin disorder is provided. The composition of the present invention may be provided in multiple embodiments, which are provided below as guidance to those skilled in the art of medical treatment or the pharmaceutical industry. Thus, the embodiments of the present invention will demonstrate a variety of nonlimiting formulations or useful combinations that may be desirable according to the skin disorder, the desired administration or treatment regimen. The compositions of the present invention include at least two compounds. One compound includes an Androgen Receptor Degradation (ARD) enhancer. The second compound can be selected from a variety of compounds known or suspected of having utility for the treatment or prevention of a skin disorder. In various embodiments, the second compound may include a bactericide, an antibiotic, an anti-microbial peptide, an anti-inflammatory compound, a compound capable of reducing one or more symptoms associated with the skin disorder, or a combination thereof. Thus, the present invention may include an ARD enhancer provided in combination with one, two, three or more compounds provided or suggested herein.

Androgen Receptor Degradation (ARD) Enhancers

Androgen receptor degradation (ARD) enhancers are compounds that modulate or increase degradation of the androgen receptor. It is believed that many skin disorders are caused or influenced by androgen-associated gene activation pathways. Current anti-androgen therapies target or interfere with receptor-ligand (androgen) binding, which only works effectively when the endogenous androgen levels are low and sometimes results in accumulation of excess androgens or can totally block androgen-regulated functions, thus further affecting other androgen associated functions. Therefore previous treatments resulting in accumulation of excess ligand may lead to undesirable treatment side effects. In contrast, the ARD enhancers of the present invention provide an effective alternative that does not induce the accumulation of endogenous ligand (androgens) in comparison to conventional therapies. In addition, ARD enhancers, their function not affected by the endogenous androgens, may reduce expression of androgen receptors, which may result in downregulation of the ligand (androgen) activity. U.S. patent application Ser. No. 12/008,124 entitled, "Compounds with (substituted phenyl)-propenal moiety, their derivatives, biological activity, and uses thereof," incorporated herein by reference, discloses a listing of compounds that are believed to have ARD enhancing activity however, the activity may vary. In preferred embodiments, the ARD enhancer is selected from the group consisting of ASC-J9, ASC-J15, ASC-Q9, ASC-Q44, ASC-Q49, ASC-Q77, ASC-Q98, ASC-Q99, ASC-Q111, ASC-Q102, ASC-Q103, ASC-Q110 or ASC-Q111, ASC-Q113, ASC-Q116, ASC-JM1, ASC-JM2, ASC-JM4, ASC-JM5, ASC-JM6, ASC-JM7, ASC-JM12, ASC-JM13, ASC-JM14, ASC-JM16, ASC-JM17, ASC-JM18 and ASC-JM19. FIG. 2 provides a structural formula of preferred ARD enhancers together with data demonstrating the relative potency of each. The potency was determined by Western Blot after incubation of LNCaP (human prostate cancer cell line) in the presence of the corresponding compound for 48 hours. Percent reduction was determined by comparison to a vehicle control.

With respect to skin disorders, androgen receptor degradation (ARD) enhancers are believed to decrease oil (sebum) secretion by sebaceous glands that are associated with hair follicles, which limits or decreases the propagation of bacteria (P. Acne). Sebum, an oily substance, is secreted by the sebaceous gland in response to stimulation of the androgen receptor. Whether stimulation of the sebaceous gland causes proliferation of sebocytes or increased production of sebum, the ligand-bound androgen receptor is believed to be a cause of increased sebum production. Therefore it is believed that enhancing degradation of the androgen receptor, i.e., avoiding activation by the ligand (androgen), may decrease sebum secretion from the sebaceous gland, reduce the proliferation of sebocytes, or inhibit or reduce sebocyte differentiation, thereby reducing the presence of sebum and reducing the presence of bacteria or bacterial infection.

Since ARD enhancers act differently from the traditional anti-androgens that act at receptor-ligand interaction, ARD enhancers may allow modulation of the sebaceous gland without substantial interference with an alternative androgen or ligand associated with AR function. A subset of compounds (ARD enhancers) are believed to induce degradation of the intracellular androgen receptor, acting via the proteosome-dependent (or ubiquitin-mediated) proteolytic pathway. Compounds such as ASC-J9 have been shown to induce degradation of the androgen receptor and affect the presence of acne. Compounds provided in FIG. 2 area also shown to decrease expression of the androgen receptor.

The ARD enhancers of the present invention are not limited to those that affect the sebaceous gland. The ARD enhancers of the present invention may be act or affect a variety of cell types, which result in the reduction of one or more symptoms associated with a skin disorder. Thus pathways are provided as examples only and are nonlimiting with respect to the present invention.

Bactericides

In another embodiment of the present invention an ARD enhancer is provided in combination with a bactericide for the prevention or treatment of a skin disorder. When used in combination, ARD enhancers may affect sebocytes or sebaceous gland while the bactericide affects the population of *P. acnes* or other strains of bacteria. Although nonlimiting, this embodiment's particular utility may be found for skin disorders such as acne, rosacea and wound healing because of likely presence of local bacterial colonies. However this embodiment will have broad utility, such as any skin disorder where the reduction of a bacterial population is desired.

Many compounds having bactericidal properties are known in the art and may be used with the present invention. Compounds may be identified according to class or according to desired properties or modes of action. Examples include sorbic acid, benzoic acid and para-hydroxybenzoic acid. One particularly desirable bactericide of the present invention is benzoyl peroxide. Benzyol peroxide includes two benzyl groups (benzaldehyde with the H of CHO removed) joined by a peroxide group. Benzoyl peroxide may be formed by the combination of sodium peroxide with benzoyl chloride (forming benzoyl peroxide and sodium chloride). Benzoyl peroxide may be administered in a gel or cream form, typically at a concentration from about 0.1% to about 20%, or about 1% to about 10%, however concentrations outside of these ranges are also encompassed by the present invention. When used in combination with an androgen receptor degradation (ARD) enhancer, the dose of benzoyl peroxide may be reduced, which reduces the frequency of skin dryness or irritation frequently associated with current benzoyl peroxide based therapies.

Antibiotics

Antibiotics are classified as either being bactericidal (compounds that kill bacteria) or bacteriostatic (compounds that prevent bacteria from dividing). Antibiotics have limited or no effect on viruses, fungi or parasites. They are relatively harmless to the host and therefore can be used to treat bacterial infections. However the frequent use of antibiotics has lead to bacterial resistant strains, among other undesirable characteristics when used alone. Classes of antibiotics that may be used in the present invention include aminoglycosides (including amikacin, gentamicin, kanamycin, neomycin, netilmicin, strepomycin and tobramycin); cabacephems (including loracarbef), cabapenems (including ertepenem, imipenem/cilastatin and meropenem); first generation cephalosporins (including cefadroxil, cefazolin and cephalexin); second generation cephalosporins (including cefaclor, cefamandole, cefoxitin, cefprozil and cefuroxime); third generation cephalosporins (including cefixime, cefdinir, cefditoren, cefoperazone, cefotaxime, cefpodoxime, ceftazidime, ceftibuten, ceftizoxime and ceftriaxone); fourth generation cephalosporins (including cefepime); gycopeptides (including teicoplanin and vancomycin); macrolides (including azithromycin, clairthromycin, dirithromycin, erythromycin, roxithromycin and troleandomycin); monobactam (including aztreonam); penicillins (including amoxicillin, ampicillin, azlocillan, carbenicillin, cloxacillin, dicloxacillin, flucloxacillin, mezlocillin, nafcillin, penicillin, piperacillin and ticarcillin); polypeptides (including bacitracin, colistin and polymyxin B); quinolones (including ciprofloxacin, enoxacin, gatifloxacin, levofloxacin, lomefloxacin, moxifloxacin, norfloxacin, ofloxacin and trovafloxacin); sulfonamides (including mafenide, prontosil, sulfacetamide, sulfamethizole, sulfanilimide, sulfasalizine, sulfisoxazole, trimethoprim and trimethoprim-sulfamethoxazole); tetracyclines (including democlocycline, doxycycline, mincycline and oxytetracycline); and others including chloramphenicol, clindamycin, ethambutol, fosfomycin, furazolidone, isoniazid, linezolid, metronidazole, nitrofurantion, platensimycin, pyrazinaminde, quinuprisitin, rifampin and sepctinomycin. Currently, the most common antibiotics used to treat acne include erythromycin, clindamycin, cotrimoxazole, tetracycline or tetracycline derivatives such as doxycycline and minocyline, each of which may be used in the present invention.

Anti-Microbial Agents and Peptides

In another embodiment of the present invention, an ARD enhancer is used in combination with an anti-microbial peptide or a compound capable of inducing or mediated the production or availability of an anti-microbial peptide. Anti-microbial peptides are typically short proteins, generally between 12 and 50 amino acids long (although larger proteins with similar properties are often classified as anti-microbial peptides and are incorporated within the scope of the present invention). These peptides often include two or more positively charged residues provided by arginine, lysine or, in acidic environments, histidine, and a large proportion (generally >50%) of hydrophobic residues. In addition to killing bacteria directly they are suspected of having a number of immunomodulatory functions that may be involved in the clearance of infection, including the ability to alter host gene expression, act as chemokines and/or induce chemokine production, inhibiting lipopolysaccharide induced pro-inflammatory cytokine production, promoting wound healing, and modulating the responses of dendritic cells and cells of the adaptive immune response. Anti-microbial peptides are thought to vary in function from affecting bacterial membranes to having intracellular targets. Nonlimiting examples of anti-microbial peptides that may be used with the present invention include, but are not limited to defensins and the cathelicidin family of polypeptides, which are characterized by a highly conserved region (cathelin domain) and a highly variable cathelicidin peptide domain. The anti-microbial effects of cathelicidins in skin are thought to be mediated by proteolysis and may involve mast cells, keratocytes and neutrophils. Kallikrein-mediated proteolysis has been proposed (FASEB. J 2006 October; 20 (12):2068-80 which is herein incorporated by reference in its entirety). It is believed that when used in combination with ARD enhancers, the cathelicidin family will be useful as a treatment for a variety of skin disorders and particularly useful in the treatment of atopic dermatitis and rosacea. It may be desirable to provide a cofactor such as Vitamin D for increased efficacy.

Vitamin A, Vitamin A Derivatives and Retinoids

In another aspect of the present invention an ARD enhancer is provided in combination with Vitamin A or a Vitamin A derivative. Vitamin A promotes healthy surface linings of the eyes, respiratory, urinary and intestinal tracts and helps the skin and mucous membranes function as a barrier to bacteria and viruses. In addition, Vitamin A helps regulate the immune system, which helps prevent or fight off infections by making white blood cells that destroy harmful bacteria and viruses. Vitamin A may also help lymphocytes fight infections more effectively.

Vitamin A derivatives encompassed within the present invention include modifications such as but not limited to alkylations, esterifications and the like and may include the addition of one or more of a variety of functional groups such as alcohols, enols, ketos, carboxyls and the like. Vitamin A derivatives may alter the anti-bacterial characteristics of Vitamin A.

Retinol is the animal form of Vitamin A. Retinol belongs to a larger family of compounds referred to as retinoids. Thus, in another aspect of the present invention a androgen receptor degradation (ARD) enhancer may be used in combination with a retinoid as a composition useful for the treatment of a skin disorder. The compositions of the present invention provide improvement over previous retinoid therapies in that at least in part, the dose of a retinoid may be reduced because of the increased combined activity with an ARD enhancer. Thus, the reduced dose will result in reduced skin irritation commonly associated with retinoid related compounds.

Anti-Inflammatory Compounds

In another aspect of the present invention an ARD enhancer is used in combination with an anti-inflammatory compound. Inflammatory compounds may be divided between steroidal anti-inflammatory compounds and non-steroidal anti-inflammatory compounds, each of which is encompassed within the present invention. Many steroids, such as glucocorticoids, reduce inflammation by binding to cortisol receptors. Often these are referred to as corticosteroid compounds.

Non-steroidal anti-inflammatory compounds include those that counteract or inhibit the cyclooxygenase (COX) enzyme. The COX enzyme synthesizes prostaglandins, which lead to inflammation. Compositions of the present invention may include non-steroidal anti-inflammatory compounds that reduce or prevent synthesis of prostaglandins, thus reducing or eliminating pain associated with inflammation.

Many herbs or compounds isolated from herbs have anti-inflammatory properties and may be used in combination with an ARD. Examples of herbs believed to have anti-inflammatory properties are hyssop, ginger, *Arnica Montana* which contains helenalin, a sesquiterpene lactone, and willow bark, which contains salicylic acid. Similarly some foods are thought to contain anti-inflammatory properties. Thus compounds isolated from foods suspected of having anti-inflammatory properties are also incorporated within the present invention. For example, capsaicin and omega-3-fatty acids are anti-inflammatory compounds found in foods and are encompassed by the present invention.

C. Compositions for the Treatment or Prevention of Hair Loss

It's the belief of the inventors that the combinations of compounds provided herein will have increased therapeutic utility when compared to current therapies for the treatment of hair loss. Thus, in one aspect of the present invention, a composition for the prevention or treatment of hair loss is provided. The compositions and treatment methods are believed to have particular use in the treatment or prevention of androgenetic alopecia. However, any hair loss condition associated with the accumulation or build up of androgen or associated with the androgen receptor can be treated or prevented, at least in part by the present invention. The compositions of the present invention may be provided in multiple embodiments, which are provided below as guidance to those skilled in the art of medical treatment or the pharmaceutical industry. Thus, the embodiments of the present invention will demonstrate a variety of nonlimiting formulations or useful combinations that may be desirable according to the medical condition, the desired administration or treatment regimen. The compositions of the present invention include at least two compounds. One compound includes an Androgen Receptor Degradation (ARD) enhancer. The second compound can be selected from a variety of compounds known or suspected of having utility for the treatment or prevention of a hair loss, baldness or androgenetic alopecia. In some embodiments the second compound is suspected of increasing or promoting hair growth. Thus, the present invention may include an ARD enhancer provided in combination with one, two or more compounds or compositions provided or suggested herein. Examples of ARD enchancers that may be used in the present invention include those provided in U.S. patent application Ser. No. 12/008,124 entitled, "Compounds with (substituted phenyl)-propenal moiety, their derivatives, biological activity, and uses thereof," which is incorporated herein by reference, In preferred embodiments, the ARD enhancer is selected from the group consisting of ASC-J9, ASC-J15, ASC-Q9, ASC-Q44, ASC-Q49, ASC-Q77, ASC-Q98, ASC-Q99, ASC-Q101, ASC-Q102, ASC-Q103, ASC-Q110 or ASC-Q111, ASC-Q113, ASC-Q116, ASC-JM1, ASC-JM2, ASC-JM4, ASC-JM5, ASC-JM6, ASC-JM7, ASC-JM12, ASC-JM13, ASC-JM14, ASC-JM16, ASC-JM17, ASC-JM18 and ASC-JM19.

Combinations of compounds or compositions provided within the present invention may be administered topically, orally, and the like as known in pharmaceutical/cosmetic arts or as described in the present invention. In some embodiments a combination of compounds are provided, wherein at least one compound is administered orally and a second compound is administered topically.

In preferred aspects of the present invention an ARD enhancer is provided in combination with a compound or composition suspected of stimulating hair growth. Thus when provided in combination, the present invention may both prevent hair loss and stimulate hair growth.

Though nonlimiting, the ARD enhancers of the present invention may be combined with compounds that interact with the androgen receptor or androgen. In some embodiments, an ARD enhancer is combined with a compound or composition that blocks androgen binding to the androgen receptor.

In some embodiments, an ARD enhancer is provided in combination with finasteride. In another embodiment, an ARD enhancer is provided in combination with flutamide or bicalutamide In another embodiment an ARD enhancer is provided in combination with minoxidil. Thus ARD enhancers may be combined with currently available or proposed treatments for hair loss.

Peptides and Oligopeptides that Promote Hair Growth

The ARD enhancers disclosed herein may be combined with peptides or oligopeptides that demonstrate or are believed to demonstrate potential activity for hair growth or prevention of hair loss. The peptides may encode domains that interact with a receptor such as an androgen receptor, cofactor such as a STAT and like.

As nonlimiting examples, ARD enhancers may be combined with peptides such as, but not limited to the following. U.S. Pat. No. 7,241,731, entitled "Oligopeptides for promoting hair growth", which is incorporated herein by reference, provides a variety of oligopeptides suspected of having beneficial activity. Peptides such as glutamine-containing peptides are also promising in the treatment or prevention of hair growth. For example U.S. Pat. No. 6,376,557, entitled "Methods of treating alopecia", which is herein incorporated by reference, discloses the use of glutamine-containing peptides used in combination with octyl butyrate.

The above peptides and oligopeptides are not intended to be limiting but instead exemplary of the compositions of the present invention that are considered useful for the treatment or prevention of hair loss when used in combination with an ARD enhancer.

Nucleotides and Oligonucleotides

The ARD enhancers of the present invention may be used in combination with nucleotides or oligonucleotides believed to increase or promote hair growth or decrease hair loss. Such nucleotides may be those that modulate the androgen receptor, cofactors of the androgen receptor and the like. Nucleotides may act upstream or downstream of the intended gene, enhance or inhibit promoter activity and the like. In some embodiments, such oligonucleotides are anti-sense oligonucleotides.

Antimicrobial Agents and Peptides

Compositions to treat or prevent hair loss may also include ARD enhancer in combination with an anti-microbial agent or anti-microbial peptide. The compounds and peptides discussed above with respect to skin disorders are also incorporated herein.

Plant Extracts

In some embodiments of the present invention, the ARD enhancer is combined with one or more plant extracts (or compositions obtained there from) that are suspected of including anti-androgenic compounds, anti-androgenic activity, or help prevent or treat hair loss. Such extracts include those obtained from plant leaves, flowers, fruits or berries, trunks, seeds and the like. The extracts may be crude extracts or may be purified such as over 50% pure, 60% pure, 75% pure, 80% pure, 90% pure or over 95% pure. Thus the extracts provided herein, their active compounds and any compounds believed to be active therewith may be used in combination with the ARD enhancers of the present invention.

In some embodiments, the extracts are obtained from saw palmetto plant, an American tree often found in the southeastern part of the United States including Georgia and Florida. Saw palmetto plant extract as well as its combination with acetyl carnitine and co-enzyme Q is disclosed in U.S. Pat. No. 6,333,057, entitled "Compositions and method for topical treatment of androgenetic alopecia"; which is herein incorporated by reference, may be used in combination with ARD enhancers. Saw palmetto plant extract is also provided in combination with African Pygeum extract and stinging nettle extract in U.S. Pat. No. 5,972,345, entitled "Natural preparation of treatment of male pattern hair loss", which is herein incorporated by reference.

The present invention also includes an ARD enhancer in combination with the following extracts or compounds isolated or purified there from. The extracts provided in U.S. Pat. No. 7,201,931, entitled "Oral compositions for treatment of scalp disorders", which is incorporated herein by reference, discloses the use of *Seranoa repens* and *Vitis vinifera*. Extracts from *Seranoa repens* were tested "in vitro" on prostate cancer cells and revealed a strong affinity to androgen receptors by displacement with radio labeled 3H-methyltrienolene. U.S. Pat. No. 6,358,541, entitled "Topical preparation for the treatment of hair loss", which is herein incorporated by reference in its entirety, discloses the use of saw palmetto berry alcohol extract containing phytosterols as useful in a low irritability solution.

The above extracts are not intended to be limiting but instead exemplary of the different sources of plant extracts that are considered useful for the treatment or prevention of hair loss when combined with an ARD enhancer.

D. Pharmaceutical and Cosmetic Compositions

The compounds of the present invention may be combined with a pharmaceutically acceptable carrier to form a pharmaceutical or cosmetically acceptable carrier to form a cosmetic. Techniques of pharmaceutical and cosmetic production are well known in the art and typically include mixing a compound or salt thereof in the presence of a suitable carrier. The compounds of the present invention may be mixed together with a single carrier or type of carrier or may be independently mixed with separate carriers. Suitable carriers for use with the compounds of the present invention include diluents, excipients, or other carrier materials, selected according to the intended form of administration and consistent with conventional pharmaceutical or cosmetic practice. Further nonlimiting examples of suitable carriers include, but are not limited to, water, physiological saline, phosphate-buffered saline, a physiologically compatible buffer, saline buffered with a physiologically compatible salt, a water-in-oil emulsion, and an oil-in-water emulsion, an alcohol, dimethylsulfoxide, dextrose, mannitol, lactose, glycerin, propylene glycol, polyethylene glycol, polyvinylpyrrolidone, lecithin, albumin, sodium glutamate, cysteine hydrochloride, and the like, and mixtures thereof. Suitable carriers can also include appropriate pharmaceutically acceptable antioxidants or reducing agents, preservatives, suspending agents, solubilizers, stabilizers, chelating agents, complexing agents, viscomodulators, disintegrating agents, binders, flavoring agents, coloring agents, odorants, opacifiers, wetting agents, pH buffering agents, and mixtures thereof, as is consistent with conventional pharmaceutical practice ("Remington: The Science and Practice of Pharmacy", 20th edition, Gennaro (ed.) and Gennaro, Lippincott, Williams & Wilkins, 2000), which is herein incorporated by reference in its entirety. The compositions of the present invention may be provided in a shampoo.

The compounds are provided in a therapeutically effective dose. The therapeutically effective dose may determined by the particular combination of compounds. The dose may vary somewhat from compound to compound, patient to patient, and will depend on the condition of the patient and route of delivery. As general guidance, a dosage from about 0.1 to about 50 mg/kg of the combined compounds or compositions may have therapeutic efficacy, while still higher or lower dosages potentially being employed. When determining a dose for a compound with an ARD enhancer, one can begin with the dose of the compound initially prescribed then preferably lower the dose.

The compounds or compositions of the present invention may be provided in a prodrug configuration, in an extended release formulation and the like. Alternatively, the compositions may be provided in an active form suitable for action without substantial modification. Similarly, the compounds or compositions of the present invention may be provided in combination with a liposome delivery vehicle. Liposomes are lyotropic liquid crystals composed mainly of amphiphillic bilayers and have the advantage of primarily comprising lecithin and cholesterol, which are materials that occur naturally in the human body. Lecithin and cholesterol are also present in the body in large amounts, and thus provide good bioacceptability. Thus, liposomes can help reduce toxicity and help deliver the drug to the site of interest. Active targeting usually involves the attachment of a ligand to the surface of the liposome or the alteration of the liposome. Ligands can include antibodies, or antibody fragments, enzymes, lectins, sugars and the like. The ligands can be attached covalently or noncovalently, but covalent attachments are more useful. Liposomes classified into three classes: multilamellar vesicles (MLVs); small unilamellar vesicles (SUVs<100 nm in diameter); and large unilamellar vesicles (LUVs>100 nm in diameter). MLVs are easily prepared and require minimal laboratory equipment. Both MLVs and SUVs have low encapsulation capacity compared to LUVs. LUVs have many advantages, including high encapsulation of water-soluble drugs, cost of lipids, and the high rate of reproducible drug release.

Other delivery vehicles used in drug delivery known, suspected or published by those skilled in the art of drug delivery are also contemplated and incorporated within the scope of the present invention. For example, nanoparticles are solid, colloidal particles having macromolecular substances that vary in size from about 10 nanometers (nm) to about 1000 nm. The compound or composition is dissolved, entrapped, adsorbed, attached, or encapsulated in the macromolecular material. Nanoparticles have been described as having the following nonlimiting compositions: a microsphere with a shell-like wall that holds the matrix, a polymer lattice that encapsulates fluid solution; and a solid particle (biodegradable or not) for surface attachment of compounds or compositions and targeting molecules. Nanoparticles are typically injected.

Co-Administration of Compounds

Although the combination of compounds may be provided in a single pharmaceutical or cosmetic, in other embodiments, the compounds of the present invention are provided as two distinct compositions and administered together or separately. The routes of administration may be the same, such as topical application of two or more compounds or may be different. For example, one compound may be provided as an oral pharmaceutical and the second as a topical pharmaceutical or cosmetic. In this example, the treatment includes application of two pharmaceuticals, one topically and one orally, which may or may not be applied concurrently or at periodic intervals or times. Thus, the compositions may vary depending on the desired treatment regimen.

E. Methods of Treating Skin Disorders

The compositions of the present invention may be used to treat, prevent or reduce undesirable symptoms from a variety of skin disorders. The skin is the largest organ of the body and obviously the most visible. Although many skin diseases are localized to a particular area or region, some are manifestations of internal disease. A variety of skin disorders have been identified and may be found in a variety of medical dictionaries, such as but not limited to Taber's encyclopedic dictionary (edition 20, 2001, FA Davis Company), which is incorporated by reference herein in its entirety. Dermatologists, physician's that specialize in the diagnosis and treatment of the diseases and tumors of the skin and appendages, may be consulted for additional potential therapeutic uses or when evaluating potential doses of compounds or compositions.

Topical applications are frequently used in treatment of the skin; however, oral medications are also common. The compositions of the present invention are adaptable for topical application, oral application, injection or any other suitable route of administration as desired or as pharmaceutically or cosmetically adaptable.

The treatment methods of the present invention include providing an individual suffering from a skin disorder and administering to the patient a therapeutically effective dose of one or more compositions of the present invention. As provided, the compositions of the present invention include at least two of the disclosed compounds, wherein one of the compounds is an ARD enhancer. Furthermore, the composition may be in the form of a pharmaceutical or a cosmetic. Similarly, a skin disorder may be prevented by administering to a patient in need thereof a pharmaceutically or cosmetically acceptable amount of one or more compositions of the present invention, wherein one of the compositions includes an ARD enhancer. The following provides a brief and nonlimiting description of skin disorders that may be treated or prevented using compounds and compositions of the present invention.

Acne

The compounds or compositions of the present invention may be used to treat or prevent acne and may accelerate the healing of lesions resulting from acne. Acne is caused in part by androgen-induced AR activation of sebaceous glands. The present invention affects sebaceous gland activation by providing an ARD enhancer capable of preventing or decreasing androgen receptor-associated activation. Inflammation and wound healing are also believed to be associated with the androgen receptor in response to ligand and may therefore be treated. Thus, the methods of the present invention may include administering a compound, pharmaceutical or cosmetic formulation to an individual in need of such treatment or prevention. Topical applications, oral and injectable forms of such formulations may be of particular interest with other routes of administration also encompassed within the present invention.

In various aspects of the present invention, methods of treating or preventing acne are provided including administering to an individual or subject in need thereof, a therapeutically effective amount of a pharmaceutical composition or a cosmetic composition. Preferably the composition reduces the amount of oil secreted and reduces the population of $P.$ $acnes$. A therapeutically effective dosage may vary somewhat from compound to compound, patient to patient, and will depend on the condition of the patient and route of delivery. As general guidance, a dosage from about 0.1 to about 50 mg/kg of the composition may have therapeutic efficacy, while still higher or lower dosages potentially being employed. Compositions or combinations of compounds that are likely to have particular utility in the treatment or prevention of acne include an ARD enhancer provided in combination with a bactericide such as benzoyl peroxide; an ARD enhancer provided in combination with at least one antibiotic; an ARD enhancer provided in combination with an anti-microbial peptide, such as a cathedicin; an ARD enhancer provided in combination with Vitamin A, a Vitamin A derivative, or a retinoid; an ARD enhancer provided in combination with an anti-inflammatory compound; or combinations thereof.

In one embodiment the pharmaceutical includes an ARD enhancer and a bactericide such as but not limited to benzoyl peroxide. In this embodiment the pharmaceutical composition is preferably provided as a cream or gel and is applied topically to the affected area(s) of the skin. There may be a single application or multiple applications. In other embodiments, the benzoyl peroxide is applied topically and the ARD enhancer orally. In another embodiment the pharmaceutical includes an ARD enhancer and an antibiotic. In this embodiment the pharmaceutical is preferably provided for oral administration. However, topical, injectible or combinations thereof may also be desired. There may be a single dose or multiple doses depending on the patient's condition. In yet another embodiment, the composition includes an ARD enhancer and an anti-microbial peptide. In still another embodiment, the composition includes an ARD enhancer and Vitamin A, a Vitamin A derivative or a retinoid. In still another embodiment the composition includes an ARD enhancer and an anti-inflammatory compound.

Atopic Dermatitis

Atopic dermatitis is a chronic form of dermatitis of unknown etiology found in patients with a history of allergy. The disease usually begins after the first two months of life and affected individuals may experience exacerbations and remissions throughout childhood and adulthood. In many cases, the family has a history of allergy. The skin lesions consist of reddened, cracked and thickened skin that can become crusty from scratching. Scaring or secondary infections may occur.

The present invention provides a method of treatment or prevention of atopic dermatitis including administering to a patient in need thereof a therapeutically effective amount of a pharmaceutical composition or cosmetic composition of the present invention. In one embodiment the pharmaceutical includes an ARD enhancer and a bactericide such as but not limited to benzoyl peroxide. In another embodiment the pharmaceutical includes an ARD enhancer and an antibiotic. In yet another embodiment, the composition includes an ARD enhancer and an anti-microbial peptide. In still another embodiment, the composition includes an ARD enhancer and Vitamin A, a Vitamin A derivative or a retinoid. In still another embodiment the composition includes an ARD enhancer and an anti-inflammatory compound.

Rosacea

Rosacea is a chronic eruption, usually localized to the middle of the face, such as the patient's nose, cheeks, forehead, around the eyes or the chin. As the condition progresses, small vascular malformations of the skin may appear and eventually the sebaceous glands of the nose may swell and produce deformities (rhinophyma). Current treatment protocols include topically applying metronizdole, clindamycin or erythromycin; oral tetracyclines and retinoids. The disease is chronic, currently used therapies can attempt to manage the condition but not cure it.

The present invention provides a method of treatment or prevention of rosacea, which includes administering to a patient in need thereof a therapeutically effective amount of a pharmaceutical composition or cosmetic composition of the present invention. In one embodiment the pharmaceutical includes an ARD enhancer and a bactericide such as but not limited to benzoyl peroxide. In another embodiment the pharmaceutical includes an ARD enhancer and an antibiotic. In yet another embodiment, the composition includes an ARD enhancer and an anti-microbial peptide. In still another embodiment, the composition includes an ARD enhancer and Vitamin A, a Vitamin A derivative or a retinoid. In still another embodiment the composition includes an ARD enhancer and an anti-inflammatory compound.

Lupus

Lupus is a condition of chronic inflammation caused by an autoimmune disease. Autoimmune diseases are illnesses that occur when the body's tissues are attacked by its own immune system. The immune system is a complex system within the body that is designed to fight infectious agents, for example, bacteria, and other foreign invaders. One of the mechanisms that the immune system uses to fight infections is the production of antibodies. Patients with lupus produce abnormal antibodies in their blood that target tissues within their own body rather than foreign infectious agents. Because the antibodies and accompanying cells of inflammation can involve tissues anywhere in the body, lupus has the potential to affect a variety of areas of the body. Sometimes lupus can cause disease of the skin, heart, lungs, kidneys, joints, and/or nervous system. When only the skin is involved, the condition is called discoid lupus. When internal organs are involved, the condition is called systemic lupus erythematosus (SLE).

The present invention provides a method of treatment or prevention of lupus, including discoid lupus and SLE, which includes administering to a patient in need thereof a therapeutically effective amount of a pharmaceutical composition or cosmetic composition of the present invention. In one embodiment the pharmaceutical includes an ARD enhancer and a bactericide such as but not limited to benzoyl peroxide. In another embodiment the pharmaceutical includes an ARD enhancer and an antibiotic. In yet another embodiment, the composition includes an ARD enhancer and an anti-microbial peptide. In still another embodiment, the composition includes an ARD enhancer and Vitamin A, a Vitamin A derivative or a retinoid. In still another embodiment the composition includes an ARD enhancer and an anti-inflammatory compound.

F. Methods of Stimulating Hair Growth and/or Preventing Hair Loss

The treatment methods of the present invention include providing a subject suffering from hair loss and administering to the subject a therapeutically effective dose of one or more compositions of the present invention. In one aspect of the present invention the hair loss is due to androgenetic alopecia. In other aspects the hair loss is not believed to be associated with androgenetic alopecia. In some aspects hair loss is associated with the accumulation of androgen or AR. In other aspects, the compositions of the present invention may be provided together with medical treatments that cause loss of hair or to reduce or eliminate such effects. In some embodiments a compound suspected of preventing hair loss is provided in combination with a compound suspected of stimulating or promoting hair growth. Multiple doses may be required and doses may change such as increase or decrease over time. Thus the ratio of ARD enhancer to second compound may also vary during treatment, such as increase or decrease over time.

As provided, the compositions of the present invention include at least two of the disclosed compounds, wherein at least one of the compounds is an ARD enhancer. Furthermore, the composition may be in the form of a pharmaceutical, shampoo, conditioner, cream, cosmetic and the like. Similarly, hair loss may be prevented or reduced by administering to a patient in need thereof a pharmaceutically acceptable amount of one or more compositions of the present invention, wherein one of the compositions includes an ARD enhancer.

Similarly, the methods of present invention include methods or treatment for stimulating hair growth or resulting in increased hair growth. The methods include administering to a subject in need thereof, a therapeutically effective amount of an ARD enhancer in combination with a second compound, such as one that is suspected of stimulating hair growth.

Androgenetic Alopecia

Androgenetic alopecia is thought to be due to the hair follicles' or surrounding tissue's sensitivity to hormones. This sensitivity is due to genetic factors and often runs in families. Androgenetic alopecia in men has been associated with several other medical conditions including coronary heart disease and enlargement of the prostate, prostate cancer, disorders of insulin resistance (such as diabetes and obesity), and high blood pressure (hypertension). In women, hair loss can be associated with an increased risk of polycystic ovary syndrome (PCOS). PCOS is characterized by a hormonal imbalance that can lead to irregular menstruation, acne, excess body hair (hirsutism), and weight gain. Hair loss in women is often correlated to a build up or increased amount of androgen.

The present invention provides a method of treatment or prevention of hair disorders, such as androgenetic alopecia or those associated with the accumulation of androgen, which includes administering to a patient in need thereof a therapeutically effective amount of a pharmaceutical composition or cosmetic composition of the present invention. The composition includes at least one ARD enhancer in combination with at least a second compound. In one embodiment an ARD enhancer is combined with minoxidil. In another embodiment an ARD enhancer is combined with finasteride or Propecia. In another embodiment an ARD enhancer is combined with anti-androgenic compound. In another embodiment, an ARD enhancer is combined with a peptide or oligopeptide.

In some embodiments, the methods of the present invention include a method of treating androgenetic alopecia including administering to a subject in need thereof a combination of compounds including a compound suspected of slowing or preventing hair loss and a second compound suspected of stimulating or promoting hair growth. At least one compound is an ARD enhancer. A compound suspected of stimulating hair growth is suspected of having hair growth stimulation activity. Nonlimiting examples include organic compounds, peptides, small peptides, nucleic acid sequences, plant extracts and the like. Such activity can be measured or determined using any suitable method that determines whether hair growth occurs.

EXAMPLES

Example 1

Overview of Enhancing Degradation of a Transcription Factor

The following examples describe non-limiting embodiments of a method of enhancing degradation of a nuclear receptor (a transcription factor), such as androgen receptor. Any mechanism that enhances degradation of the nuclear receptor of interest can be used, including, but not limited to, interfering with translocation of the nuclear receptor into the nucleus or retaining the nuclear receptor in the cytoplasm of a cell, exposing a motif within the nuclear receptor able to induce protease activity, increasing activity of a protease capable of specifically degrading the nuclear receptor, inhibiting the stabilization of a nuclear receptor, reducing the solubility of the nuclear receptor, activating a pathway able to degrade the nuclear receptor, increasing ubiquination of the nuclear receptor, increasing/decreasing phosphorylation of the nuclear receptor by an appropriate kinase, inducing apoptosis, or reducing an interaction between a nuclear receptor and a cofactor able to stabilize the nuclear receptor. In this particular example, the nuclear receptor of interest is the steroid hormone receptor, the androgen receptor.

Various methods and assays can be used to detect down regulation of nuclear receptor transcriptional activity and therefore degradation of the nuclear receptor of interest, or to detect the downstream effects of such degradation. For example, assays used to detect the down regulation of the androgen receptor may be used at least in part to detect degradation of the androgen receptor. Non-limiting examples of such methods and assays, as applicable to the androgen receptor, are described in general below.

Detection of AR Degradation Using Western Blot Analysis

A Western blot method suitable for detecting degradation of the androgen receptor (AR) has been previously described (Su et al., 1999). Briefly, cells (for example, LNCap cells) are harvested either in 2× sodium dodecyl sulfate (SDS) loading buffer or in radioimmunoprecipitation assay (RIPA) lysis buffer (see "Antibodies: A Laboratory Manual", E. Harlow and D. Lane, Cold Spring Harbor Laboratory, 1988) containing 10 micrograms/milliliter of benzamidine, 10 micrograms/milliliter of trypsin inhibitor, and 1 millimolar of phenylmethylsulfonyl fluoride (PMSF). Total protein (40 micrograms/sample, or as desired) from cell lysate is separated on a SDS-PAGE gel. After separation, proteins are transferred from the gel to a nitrocellulose membrane following standard Western blot procedures. The membrane is blocked with a suitable blocking agent (such as 10% non-fat milk in phosphate-buffered saline supplemented with 0.1% Tween-20 (PBST)) to reduce non-specific binding overnight. The membrane is incubated with a suitable primary antibody specific for human AR (for example, anti-human AR from BD-PharMingen) at 4 degrees Celsius overnight or at room temperature for 2 hours. The membrane is rinsed with PBST three times, 10 minutes each time, and then incubated with an appropriate secondary antibody (for example, an enzyme-labeled secondary antibody, such as horseradish peroxidase-conjugated secondary antibody) for 1 hour at room temperature. The membrane is rinsed with PBST, and a suitable visualization procedure is used to detect the secondary antibody (for example, horseradish peroxidase can be detected with a colorimetric substrate or by a chemiluminescent substrate such as that provided by the enhanced chemiluminescence (ECL Plus) kit from Amersham). The secondary antibody signal, as a measure of the amount of androgen receptor protein on the blot, can be normalized to the total amount of protein loaded for each sample by stripping the membrane following the manufacture's recommendations and re-incubating the membrane with an appropriate antibody (such as an antibody to beta-actin, Sigma). Quantification of the protein signals can be carried out by densitometry, using appropriate software (ImageJ software from the National Institutes of Health).

Compound that Inhibits AR Activity and Tumor Cell Growth

In the non-limiting examples, compounds were used to degrade the androgen receptor (AR) in cells. Non-limiting examples of compounds that were tested for their ability to degrade AR include compounds, whose structures and preparations are described in Ohtsu et al. (2002), *J. Med. Chem.*, 45:5037-5042 and Ohtsu et al. (2003) *Bioorg. Med. Chem.*, 11:5083-5090, which are incorporated by reference in their entirety herein. As examples, the compounds ASC-J9 were tested on cultured cells. ASC-J9 is a synthetic compound (trivial name, dimethylcurcumin), and has the structure 5-hydroxy-1,7-bis(3,4-dimethoxyphenyl)-1,4,6-heptatrien-3-one; it is obtainable, for example, by permethylation of natural curcumin with diazomethane.

Example 2

Enhancing Degradation of a Nuclear Receptor

This describes a non-limiting example of methods and assays useful in studying the effects of degradation of a nuclear receptor. In this particular example, a compound known to enhance degradation of the nuclear receptor, androgen receptor (AR), was examined for its effects on AR activity and on cell proliferation. One of the major tasks in cancer management is to control or slow tumor proliferation. Androgen and AR plays a significant role in stimulating prostate cancer cell proliferation, and thus, modulation of AR activity by AR degradation could serve as a useful means to delay or control prostate cancer progression.

Detection of Cell Growth and Androgen Receptor Expression in LNCaP Cells

Growth Assay

LNCaP cells express an endogenous mutant AR that is found in prostate cancer patients. This clinically relevant cell model was used to study ASC-J9's effect in suppressing prostate cancer cell growth. Cells were plated, at a density of approximate $6.5 \times 10^4$ cells/well, into 6-well tissue culture dishes. Two days later, the complete medium was aspired and 10% charcoal/dextran-treated (hormone depleted) serum-containing medium was added. Test compound, ASC- J9 was then added to the medium at a final concentration of 5 μM with or without 1 nM of DHT. For vehicle control, the same amount of DMSO was added into the medium. For the subsequent 5 days, the medium was aspirated once per day, and replaced with fresh medium containing test compound and/or DHT. At designated times, a portion of cells was harvested by trypsinization, and cell count was performed using a hemacytometer.

Figure 4:
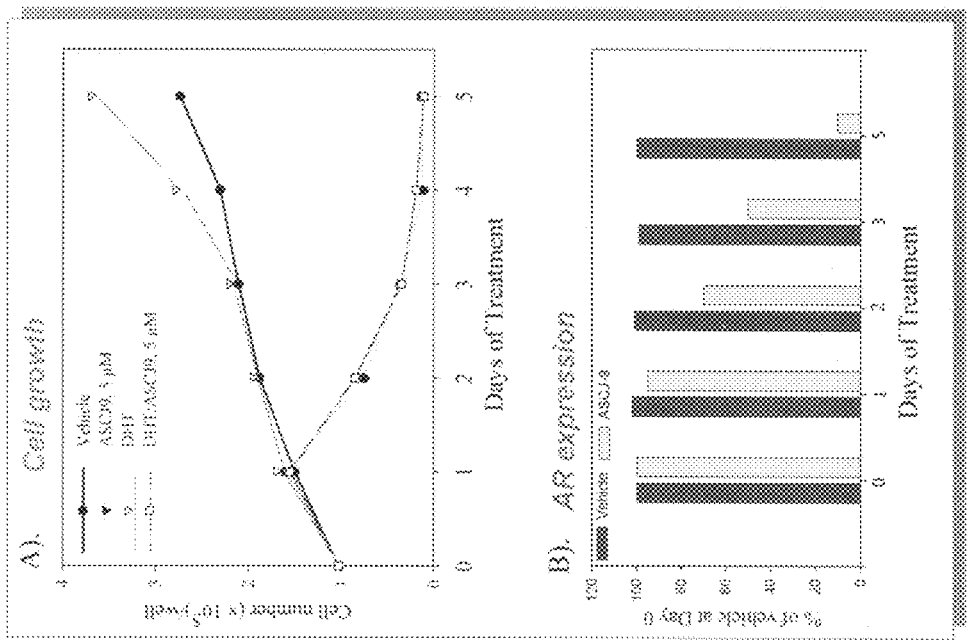
FIG. 4 depicts a graphical representation of cell growth (proliferation) and androgen receptor expression levels in ASC-J9-treated LNCaP cells. LNCaP cells were plated and incubate for two days. ASC-J9 was added to the medium at a final concentration of 5 uM with and without DHT.

During a 5-day experimental duration, the cell number in vehicle control-treated wells steadily increased (FIG. 4A). On Day 1, the cell number of ASC-J9-treated wells was comparable to that of vehicle control, but starting from Day 2, there was a marked decrease in cell number in these wells. At the end of a 5-day incubation, only a minimal number of viable cells were found in the ASC-J9-treated wells.

ASC-J9's effect on prostate cancer cell growth was further assessed in the presence of androgen, DHT. As expected, DHT up-regulated LNCaP cell growth; a raise in cell number per well became visible after the cells were allowed to be incubated with this male hormone for 4-5 days. In the presence of DHT, ASC-J9 still displayed a good potency to decrease LNCaP cell growth; the magnitude of cell growth decrease in the presence or absence of DHT was actually comparable. Based upon the above findings, it is concluded that ASC-J9 can effectively nullify prostate cancer cell growth in the presence or absence of male hormones. ASC-J9 may be useful as a drug candidate for prostate cancer disease management.

Western Blot Analysis of AR Expression

AR is the key factor in regulating prostate cancer cells' response to androgens. We examined whether ASC-J9 influences the steady-state level of AR and whether the reduction of AR correlate to the growth of LNCaP cells. LNCaP cells from the above described experiment were harvested at designated times, cell lysate was prepared for Western blot analysis as described previously. A color detection method was subsequently employed to examine AR and actin protein signals in the membranes, and the resultant protein signals were quantitated by densitometry. In FIG. 4B, normalized AR signals (as relative to actin protein) are reported, which were expressed as a percentage of baseline (Day 0) value.

The results show that the endogenous level of AR steadily declined in LNCaP cells treated with ASC-J9. AR reduction was first observed after 2 days of continuous incubation with ASC-J9, and at the end of the 5-day incubation, only ~10% initial level of AR remained in the treated cells. It is noteworthy that there is a correlation between the decrease in cell number and in AR reduction after ASC-J9 incubation. This information strongly suggests that ASC-J9 may act, at least in part, through the AR reduction mechanism to down-regulate LNCaP cell growth.

Additional compounds were tested for their ability to reduce AR expression in LNCaP cells. The results are summarized in FIG. 2. LNCaP cells were incubated for 48 hours in the presence of each test compound then analyzed by Western Blot. The relative potency was assessed for each compound by determining the percent AR reduction compared across various concentrations to vehicle control. The indications are as follows:

TABLE 1

| Relative potency | 0.5 μM | 1 μM | 2.5 μM | 5 μM | 7.5 μM |
|---|---|---|---|---|---|
| +++++ | 10-40% | 50-70% | 70-100% | | |
| ++++ | 0 | 10-20% | 30-60% | 70-100% | |
| +++ | 0 | 0 | 10-20% | 30-60% | 70-100% |
| ++ | 0 | 0 | 0 | 10-40% | 60-90% |

FIGS. 3A and 3B depict photographs of Western Blot data of compounds ASC-Q49, ASC-Q103, ASC-JM12, ASC-JM14, ASC-77, ASC-JM4 and ASC-JM5. The corresponding compounds was added to LNCaP cells and allowed to incubate for 48 hours prior to analysis. The results demonstrate Androgen Receptor (AR) protein expression is reduced upon exposure to the ARD enhancers.

In Vivo Xenograft Tumor Growth Assay

Figure 12:
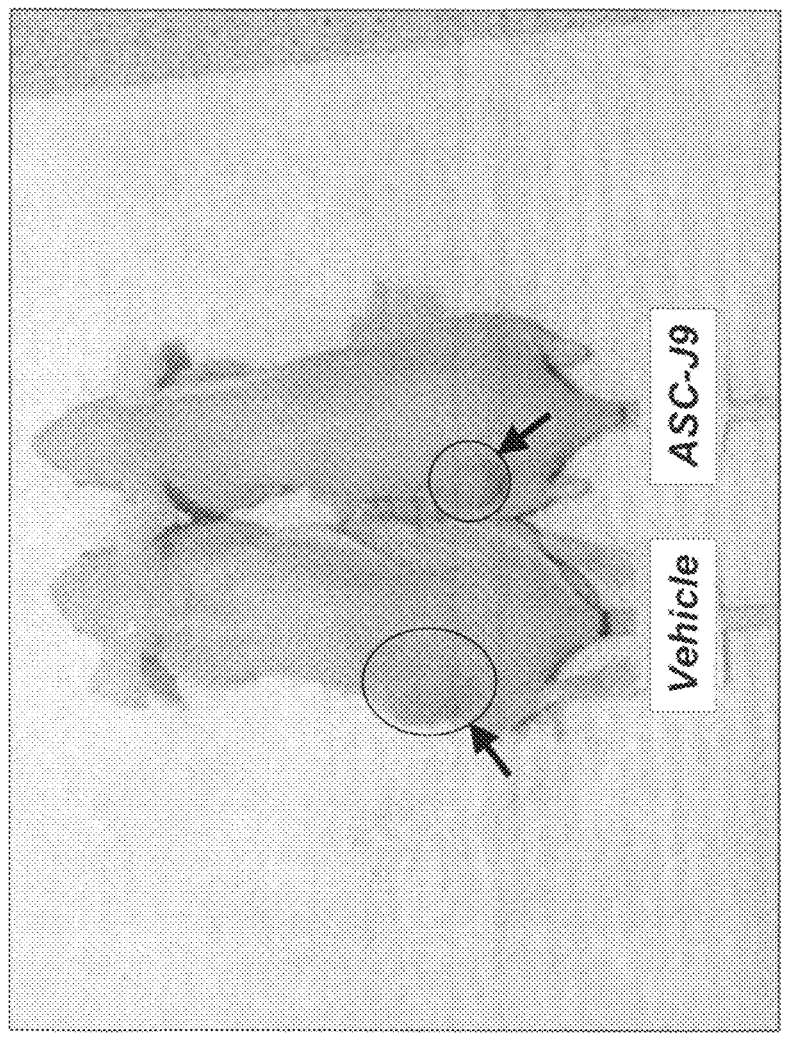
FIG. 12 depicts a photograph demonstrating the reduction of LNCaP growth in nude mice. The ASC-J9 mouse received 100 mg/kg, 3 times per week via IP injection for 7 weeks. The tumor weight reduced 75% and serum PSA level reduced 90% as compared to the vehicle control animal.

In the related in vivo studies, LNCaP human prostate tumor cells are xenografted into nude mice by subcutaneous injection ($2 \times 10^6$ per site). Mice are subsequently treated, by intraperitoneal injection, with either the vehicle solution as control or the test compounds (ASC-J9 at a dose of 100 milligrams per kilogram body weight), three times a week for 7 weeks. Tumor volume is measured twice a week over the next 7 weeks. Treatment with compounds such as ASC-J9 for a sufficient period of time (for example, from between 2 weeks to a few months) is expected to result in a significantly reduced rate of tumor growth. Data in FIG. 12 show two nude mice received xenografted LNCaP tumor and one treated with vehicle solution (left) and the other with ASC-J9 (right). A significant reduction in tumor size and PSA content in plasma were detected in animal received ASC-J9 treatment. Such results can be taken as a strong indication that the suppression of AR activity and the resulting reduction of tumor growth induced by AR-degrading compounds such as ASC-J9, may be translated into a practical use for treating or preventing diseases and disorders related to AR activity, such as prostate and other cancers.

Example 3

Specificity of Steroid Hormone Receptor Degradation in Different Cell Lines

This describes a non-limiting example of specific degradation of nuclear receptors (in this case, steroid hormone receptors) in various cell lines. Two representative tumor cell lines: the human prostate cancer cell line, LNCaP, and the human mammary adenocarcinoma cell line, T47D, were used to test the specificity of effects of ASC-J9 on the androgen receptor and other intracellular proteins and receptors.

Human prostate cancer LNCaP cells and T47D cells were plated at a density of $7 \times 10^5$ cells per 60 millimeter tissue culture dish in Richter's Improved MEM Insulin (RPMI) medium containing 10% FBS. The medium was changed to RPMI or DME medium containing 10% charcoal-stripped serum 24 hours later to deplete cellular androgens or estrogens. After another 24 hours, treatment with the test compounds began. The test dose of ASC-J9 was 1, and 5 and micromolar. LNCap cells also received dihydrotestosterone (DHT) (3 nanomolar). Control cells received a corresponding amount of the vehicle, dimethylsulfoxide (DMSO) (<0.04%) for an equivalent exposure time. Cells were incubated with ASC-J9 for 24 hours, and were lysed in 250 microliters of 1×SDS/PAGE loading buffer. Approximately 40 micrograms of total cellular protein was loaded in each lane of a pre-cast gel (NuPAGE, Invitrogen). Protein separation and transfer were performed following the manufacturer's instructions.

For the LNCaP cell lysates, androgen receptor (AR) protein was visualized by incubating the resultant membranes with an anti-AR antibody (BD-PharMingen), followed by chemiluminescence detection (ECL Plus, Amersham). To examine the effect of the test compounds on other cellular proteins, several identical gels were prepared and the resulting membranes incubated with antibodies specific for progesterone receptor (PR), estrogen receptor beta (ER beta), peroxisome proliferator-activated receptor alpha, beta or gamma (PPARα, β or γ), retinoid X receptor alpha (RXRα), the 70-kDa heat shock protein (hsp70), and a cytoskeletal protein, actin. Antibodies for PR and other nuclear receptors were obtained from Santa Cruz Biochemicals, while the antibodies for hsp70 and actin were from StressGen and Sigma, respectively. The resultant protein signals were quantified using densitometry and NIH ImageJ software.

Figure 5:
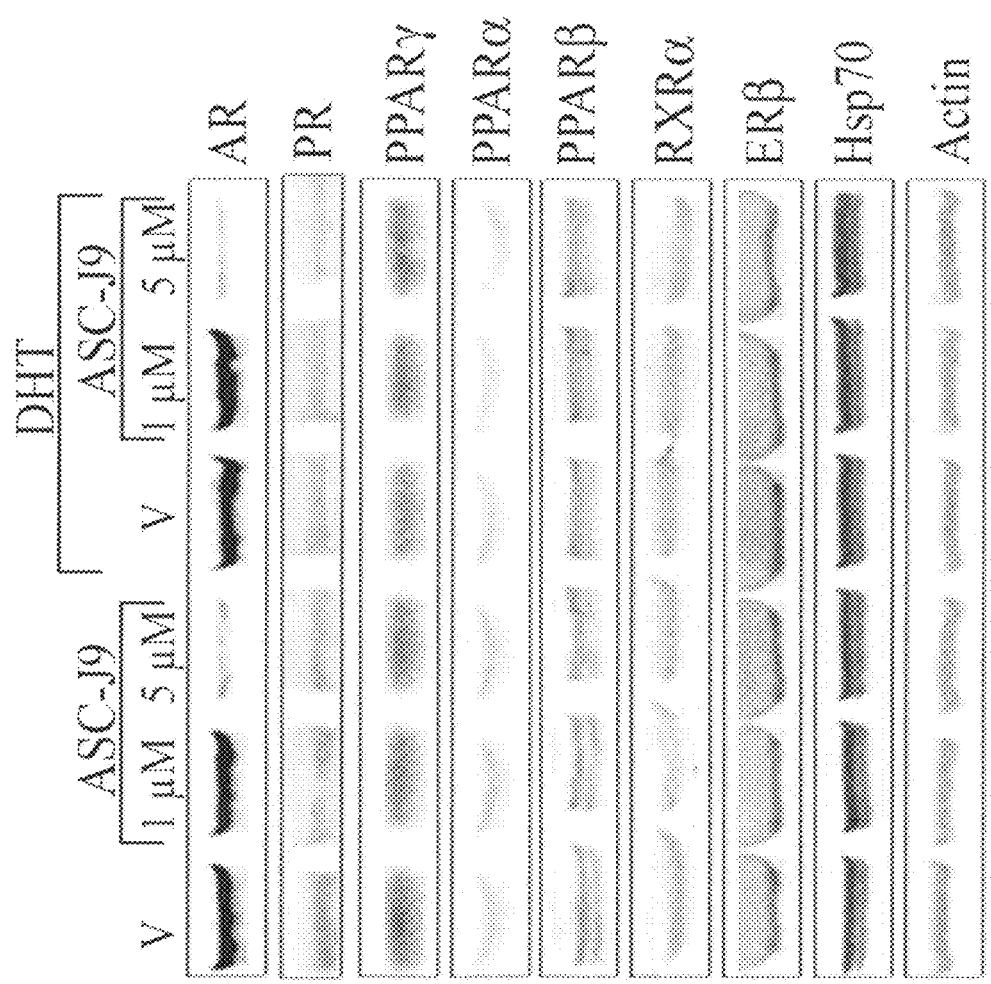
FIG. 5 depicts a western blot analysis of LNCaP cell lysates that were cultured with ASC-J9 for 48 hr. in the presence or absence of DHT. Data demonstrated that ASC-J9 reduced AR, PR proteins expression regardless in the presence or absence of DHT, but did not affect expression of other proteins, such as ER, PPAR, RXR, HSP and Actin.

The Western blots of LNCaP cell lysates are shown in FIG. 5. Incubating LNCaP cells with ASC-J9 (1 or 5 micromolar, 24 hours), in the presence or absence of DHT, significantly decreased the cellular concentrations of AR and to a lesser degree in progesterone receptor, but did not substantially affect the other tested nuclear receptors or proteins.

Figure 6:
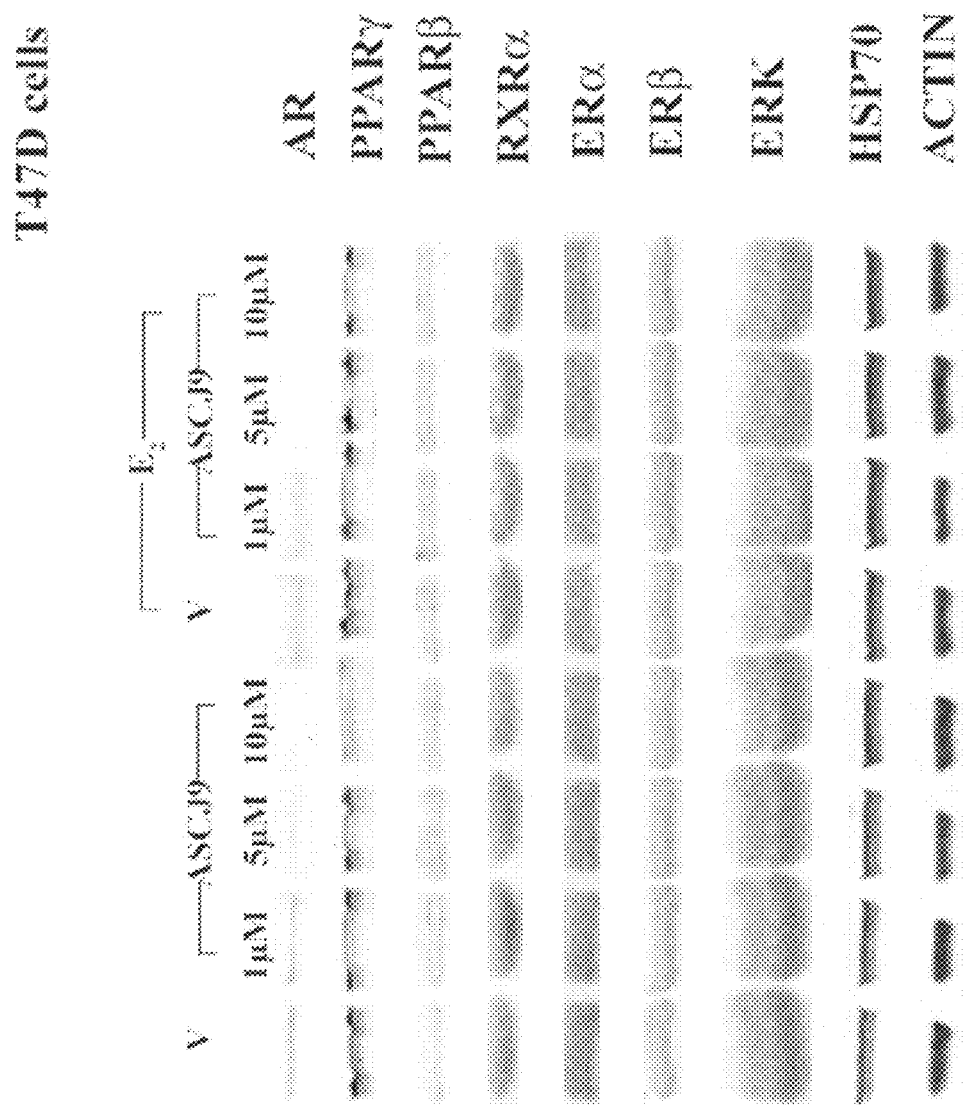
FIG. 6 depicts a western blot analysis of T47D (a human breast cancer) cell lysates demonstrating the specificity of ASC-J9's ability to degrade the androgen receptor. Data demonstrated that ASC-J9 selectively reduced expression of androgen receptor (AR). The expression of other receptor proteins, Peroxisome proliferator-activated receptors gamma and beta (PPARγ, PPARβ), retinoid X receptor alpha (RXRα), estrogen receptor alpha and beta (ERα and Er$_β$), extracellular signal-related kinase (ERK), heat shock protein 70 (HSP70) and actin, was not affected.

The Western blots of T47D cell lysates are shown in FIG. 6. Incubating T47D cells with ASC-J9 (5 or 10 micromolar) in the presence or absence of estrodial (E2) decreased the cellular concentrations of AR but not other receptor proteins similarly to the observations made in LNCaP cells.

Example 4

Enhancing Degradation of a Transcription Factor in the Presence of a Protein Synthesis Inhibitor To determine whether the observed reduction of AR protein levels was due to protein degradation rather than inhibition of AR protein synthesis, a second set of three replicate experiments was performed. In these experiments, the protein synthesis inhibitor cycloheximide (CHX) was used to prevent the cells from synthesizing new proteins. In the absence of new AR protein synthesis, any alterations in AR levels would be mainly attributable to protein degradation. LNCaP cells were cultured in the presence and absence of ASC-J9 (20 micromolar) and in the presence and absence of cycloheximide (15 micrograms/milliter). Cells were then incubated for 0, 3, 6 and 12 hours before harvesting and analysis of AR levels by Western blot.

Figure 7A:
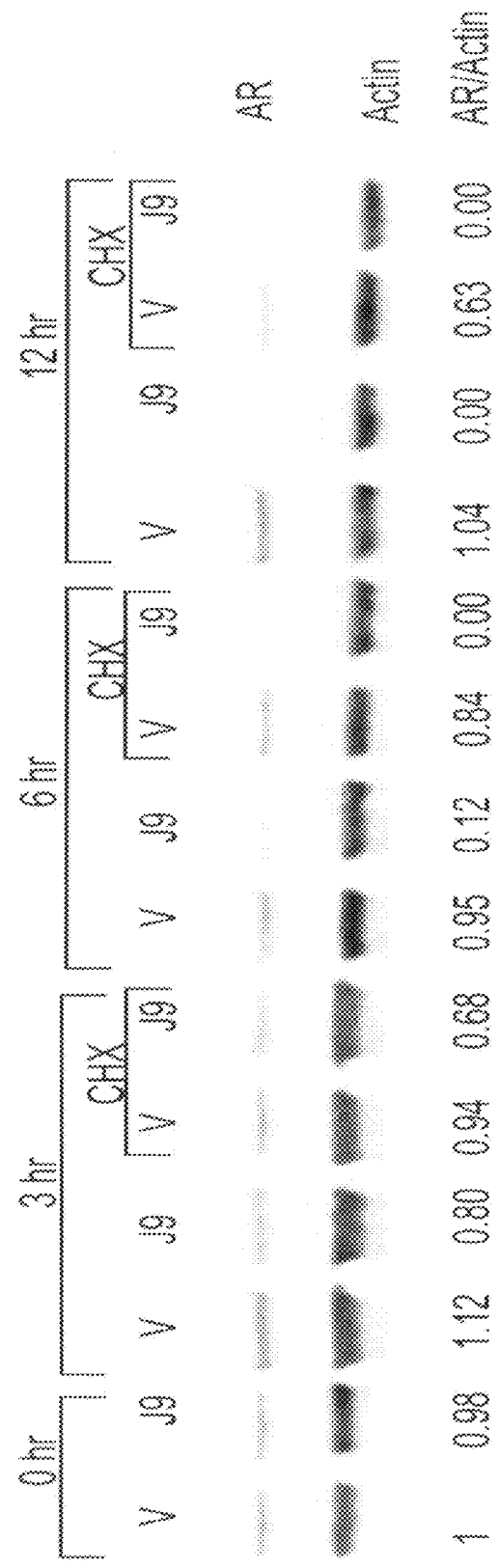
FIG. 7A depicts a western blot analysis of LNCaP cell lysates upon exposure to compound ASC-J9 and cyclohexamide, a protein synthesis inhibitor. The reduction of androgen receptor over time in the presence of a protein synthesis inhibitor indicates ASC-J9 enhances degradation of AR protein.

A representative western blot from an experiment is depicted in FIG. 7A. A reduction of endogenous AR concentration in the control cells was detected within 3 hours of treatment with cycloheximide, suggesting that de novo AR synthesis contributes to the steady-state level of this receptor. The observed reduction of existing AR protein indicates that the test compound (ASC-J9) enhanced or increased the degradation of existing AR protein (and thus decreased AR activity) within 4 hours or less.

Figure 7B:
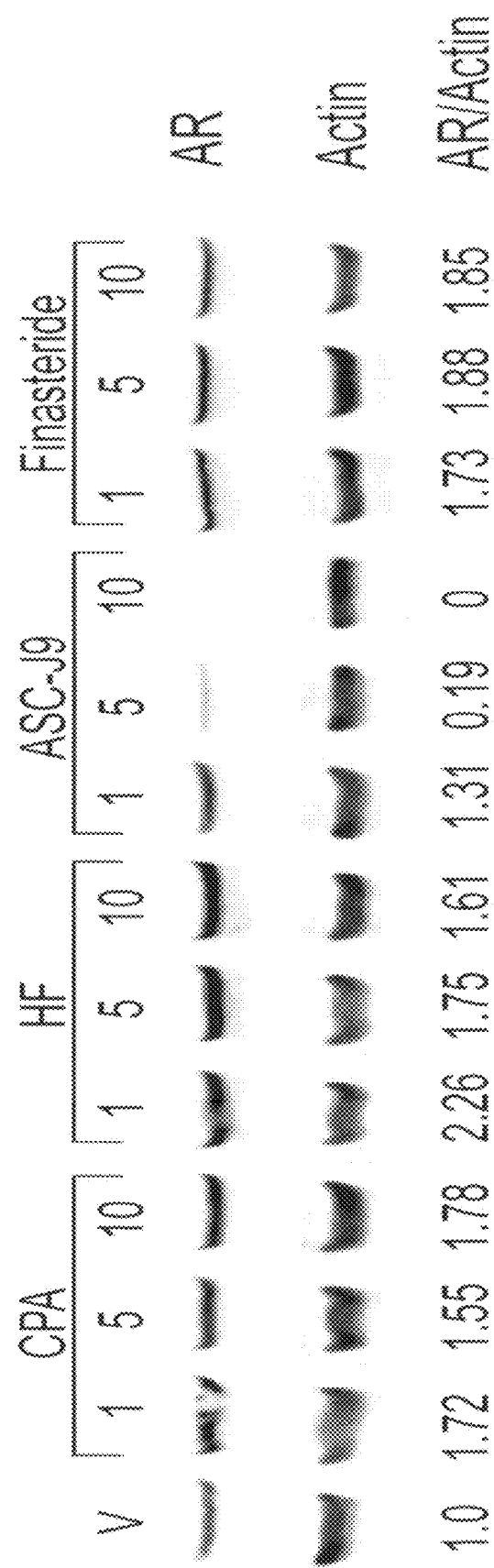
FIG. 7B is a western blot demonstrating that ASC-J9 is the only anti-androgen that is capable of reducing AR protein expression, and not the conventional anti-androgens, such as CPA (cyproterone acetate), HF (hydroxyflutamide), or finasteride.

To compare the effect of ARD enhancers with conventional anti-androgens on their activity in reducing AR expression, ASC-J9 and conventional anti-androgens CPA (Cyproterone acetate), HF (hyroxyflutamide) and Finasteride were tested on LNCaP cells. FIG. 7B, LNCaP cells were cultured in the presence of ASC-J9, CPA, HF or Finasteride for 48 hours. Cells were then harvested and AR protein was quantified by Western blot. Only ASC-J9 treatment resulted in decreased AR protein, indicating ASC-J9 induces degradation of the androgen receptor while conventional anti-androgens, CPA, HF and Finasteride, do not.

Example 5

Degradation of a Mutant Androgen Receptor

This describes a non-limiting example of degradation of a mutant nuclear receptor in a model of a human disease associated with accumulation of the mutant nuclear receptor. In this specific example, a model of Kennedy disease is investigated. Kennedy disease or spinobulbar muscular atrophy (SMBA) is a neurodegenerative disease caused by an androgen receptor mutation consisting of an abnormally long polyglutamine expansion in the N-terminus region of the AR gene. Experimental transfection of cells with a mutated AR having expanded polyglutamine (poly Q49 (49 repeat of polyglutamine)) has been shown to be associated with a decreased transactivational function and, in some cases, intranuclear inclusions of misfolded AR proteins (Chamberlain et al. (1994) *Nucleic Acid Res.*, 22:3181-3186). This intranuclear accumulation of abnormal AR is cytotoxic, triggering neuronal cell death, consistent with the in vivo pathology of Kennedy disease.

Figure 8A:
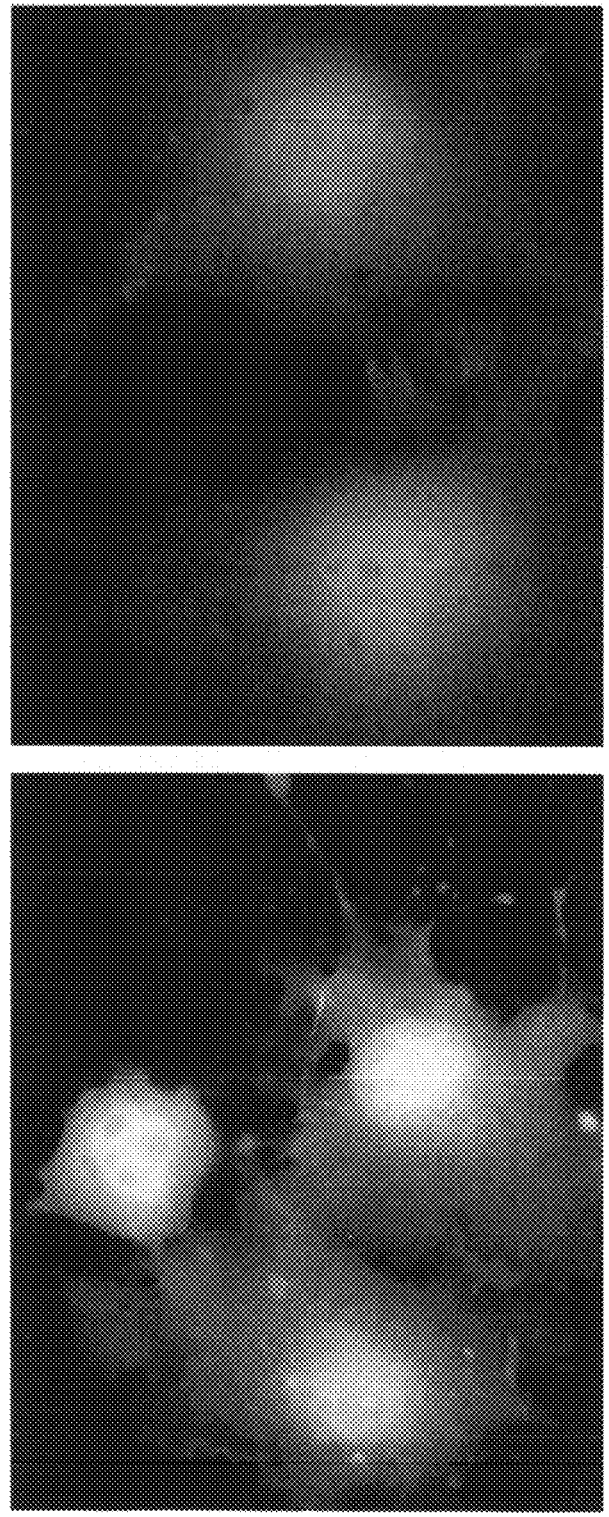
FIG. 8A depicts fluorescence micrographs of monkey kidney COS-1 cells transfected with the plasmid GFPAR (which contained a green fluorescent protein gene and wild type androgen receptor gene). Transfected cells were treated with vehicle only (control) or with the test compound ASC-J9. Micrographs were taken under fluorescent imaging conditions for green fluorescent protein (GFPAR). Control cells contained dense quantity of fluorescence in nucleus (i.e., the wild type AR) and dimmer fluorescence in the cytoplasm. Cells that had been treated with ASC-J9 dim fluorescent was detected in both nucleus and cytoplasm, indicated ASC-J9 reduces (or degrades) the expression of AR.
Figure 8B:
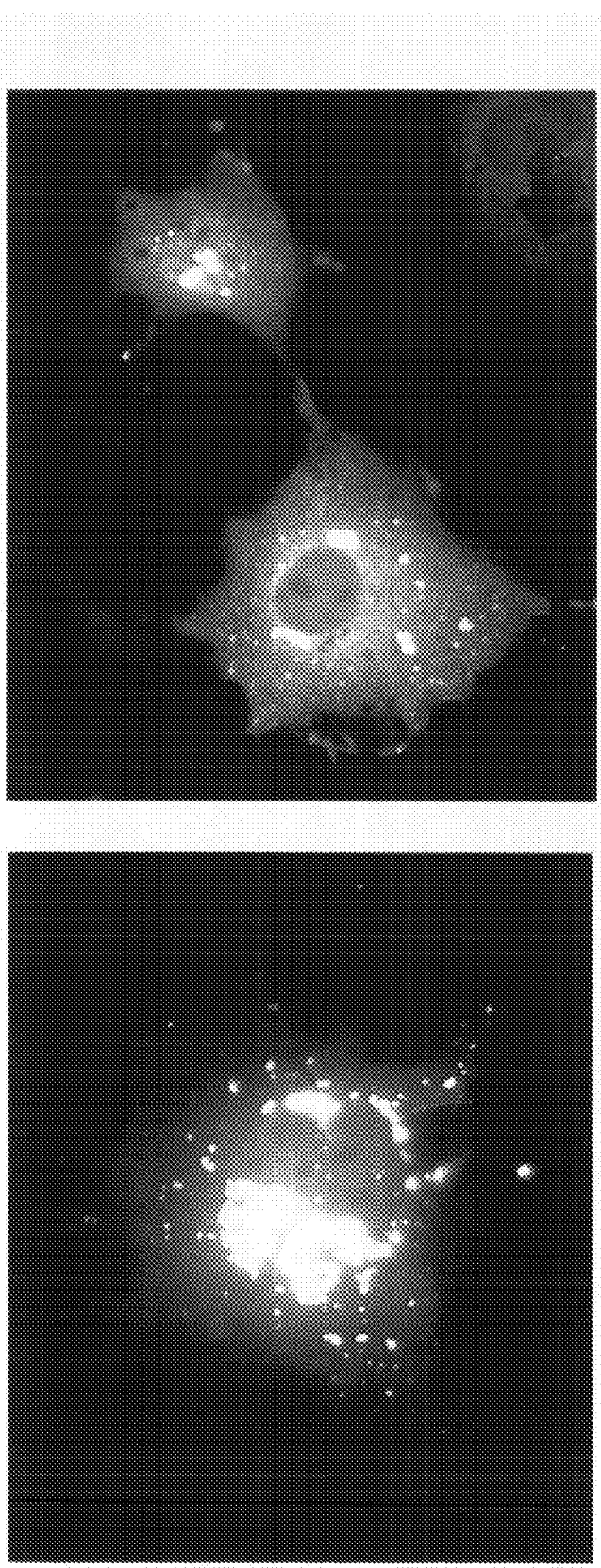
FIG. 8B depicts fluorescence micrographs of monkey kidney COS-1 cells transfected with the plasmid GFPARQ49 (which contained a green fluorescent protein and a mutant androgen receptor poly Q49 gene) as described in detail in Example 5. Transfected cells were treated with vehicle only (control) or with the test compound ASC-J9. Micrographs were taken under fluorescent imaging conditions for green fluorescent protein (GFPARQ49). Control cells contained large amounts of fluorescent inclusions or aggregates (i.e., the aggregated mutant poly Q49) in cytoplasm. Cells that had been treated with ASC-J9 contained substantially smaller amounts of fluorescent inclusions, suggesting that the expression of mutant poly Q49 androgen receptor was inhibited or degraded by ASC-J9 treatment.

Monkey kidney COS-1 cells were plated at a density of $3 \times 10^4$ cells per 0.5-milliliter volume onto alcohol-cleaned and sterilized cover slips placed in 35-millimeter suspension culture dishes containing Dulbecco's modified Eagle's (DME) medium containing 10% FBS. The cells were transfected with plasmids containing the wild type AR (GFPAR) or poly Q49 (plasmid GFPARQ49) mutant androgen receptor and green fluorescent protein (GFP) as a reporter. For each coverslip, 12.3 microliters SuperFect was added to 3.075 micrograms plasmid in 102.5 microliters DME medium (to give a 1:4 ratio of DNA to SuperFect reagent); the mixture was vortexed briefly, and the complex allowed to form over 15 minutes. Each mixture then received 897 microliters CD/DME and was mixed gently. The resulting 1-milliliter volumes were added to the dishes containing the coverslips (final plasmid concentration was 3.02 micrograms per dish). Cells were allowed to incubate with the transfection solution for 5 hours, then the medium was changed to fresh 1.5 milliliters CD/DME medium with either vehicle (DMSO) only added or ASC-J9 (final concentration 5 micromolar). Twenty-four hours after transfection termination, the medium was changed again to fresh CD/DME medium (with or without 1.5 nanomolar DHT), and either vehicle or ASC-J9 added (final concentration 5 micromolar). Twenty-four hours after changing medium, the medium was removed and the cells fixed with 1% formaldehyde in phosphate-buffered saline (PBS) for 1 hour at room temperature. The formaldehyde was removed and the fixed cells washed with PBS three times, and the coverslips then allowed to dry. Coverslips were marked to indicate the treatment scheme and hydrophobic circles made with a wax pencil around the cells. Each coverslip was stained with 200 microliters of propidium iodide (0.7 micrograms per milliliter in water) for 5 minutes at room temperature, then rinsed three times with PBS. The coverslips were air-dried, mounted on slides with a glycerol-based mounting agent, and stored at 4 degrees Celsius if necessary prior to observation with fluorescence microscopy. Representative micrographs showing COS-1 cells transfected with the GFPAR and GFPAR poly Q49 plasmids are depicted in FIGS. 8A and 8B. As shown in the micrographs, transfected cells expressed the plasmid as shown by the fluorescent reporter protein GFP. Control cells contained large amounts of fluorescent inclusions or aggregates (FIG. 8B). Cells that had been treated with ASC-J9 contained substantially smaller amounts of fluorescent inclusions, suggesting that the expressed mutant poly Q49 androgen receptor was degraded by ASC-J9 treatment.

Example 6

Reduction of Sebaceous Glands in Rats by Degradation of the Androgen Receptor

In this example, the test compounds ASC-J9, which were shown in the previous examples to ameliorate the effects of the androgen receptor-activated pathway, specifically by inducing degradation of the androgen receptor, and to be effective in treating acne in human subjects, were used to reduce sebaceous glandular lobe size in an animal model. Effective reduction of sebaceous glands by topical treatment may be useful in treating skin conditions such as acne. Fuzzy rats were used in this animal model as described in Ye et al. (1997) *Skin Pharmacol.*, 10:10288-10297, which is incorporated by reference in its entirety herein.

Topical creams were prepared as later described in EXAMPLE 12. The test creams contained ASC-J9 (25 micromolar) or a control cream with only vehicle added was also prepared. The test or control creams were applied using a cotton swab to the dorsal skin of the animal, once daily, over a period of 8 weeks. Animals were then sacrificed and skin samples collected for microscopic examination. Commercial hair remover was applied to the dorsal surface of the euthanized animals. After 5 minutes, the hair remover and hairs were removed with a tissue. The area was thoroughly cleaned with 75% isopropyl alcohol. A 4-millimeter skin punch was used to remove skin tissue samples, which were incubated for 2 to 3 hours in a ethylenediaminetetraacetate (EDTA, 17 millimolar), sodium phosphate (0.1 molar, pH 7.4) solution at 37 degrees Celsius. The epidermis was carefully separated from the dermis and stored in 10% phosphate-buffered formalin. Prior to microscopic examination, the samples were mounted on glass slides. Areas of well-preserved glandular lobules were selected for microscopic imaging. Edges of the glandular lobes were traced and the areas of the traced lobes obtained with Image J software (National Institutes of Health).

Results are shown in FIG. 9 and FIG. 10. As shown in FIG. 9, the brown color of skin and bands of sebaceous glands were reduced within 4-5 weeks in the Fuzzy rats treated with ASC-J9. As shown in FIG. 10A-C, topical treatment of male rats with compounds ASC-J9 (200 μM) resulted in a significant reduction in the size of the sebaceous gland, though not to the extent caused by castration. In FIG. 10D, data showed topical treatment with the vehicle only (control cream) did not produce a significant change in glandular lobe size. Topical treatment with the various concentrations of ASC-J9 resulted in a significant reduction in the size of the sebaceous glandular lobe (panel A), though not to the extent caused by castration, but are better than the conventional anti-androgen flutamide. FIG. 10E (labeled panel B), depicts representative data showing that ASC-J9 applied to skin significantly reduced the size of ducts of sebaceous glands in male Fuzzy rats comparable to the castration effect and better than flutamide.

Example 7

Treatment of Androgen-Induced Alopecia in an Animal Model by Degradation of the Androgen Receptor This example describes the treatment of a nuclear receptor-related disorder in a subject by degradation of the nuclear receptor. In this example, the nuclear receptor is the steroid hormone receptor, the androgen receptor. The nuclear receptor-related disorder is alopecia (hair loss or baldness), which is known to be affected by the androgen receptor. In this example, the test compound ASC-J9, which was shown in the previous examples to ameliorate the effects of the androgen receptor-activated pathway, specifically by inducing degradation of the androgen receptor, is used to treat hair loss in an animal model.

C57BL/6J mice were used in this animal model for hair loss and regrowth (Uno et al. (1990) *J. Cutaneous Aging & Cosm. Derm.*, 1:193, which is incorporated by reference in its entirety herein). Six-week-old male mice (6 to 7 animals per group) were shaved with an electric clipper, and then treated with a hair-removal cream for 1 to 2 minutes. Animals that were found to have a dark skin color after shaving, indicating that they were in anagen phase where there is active growth of hair follicles, were excluded from the study. One day after hair removal, a first group of animals each received 100 microliters of a 1% testosterone solution in ethanol, applied topically to the shaved area, once each morning for twenty consecutive days. A second group of animals each received 100 microliters of vehicle (ethanol) alone, applied topically to the shaved area, once each morning for twenty consecutive days. The first group of mice (testosterone-treated) were divided further into a control group and a treatment group. Also beginning one day after hair removal, each mouse in the control group received 100 microliters of a control solution (60% ethanol, 20% propylene glycol, and 20% water) and each mouse in the treatment group received 100 microliters of the test compound, ASC-J9 (0.02% in the same 60% ethanol, 20% propylene glycol, and 20% water solution), applied topically to the shaved area, once each afternoon for twenty consecutive days. Hair re-growth in the shaved areas was observed and photographed at 0, 4, 8, 11 and 14 days after beginning of the topical treatments.

Figure 11A:
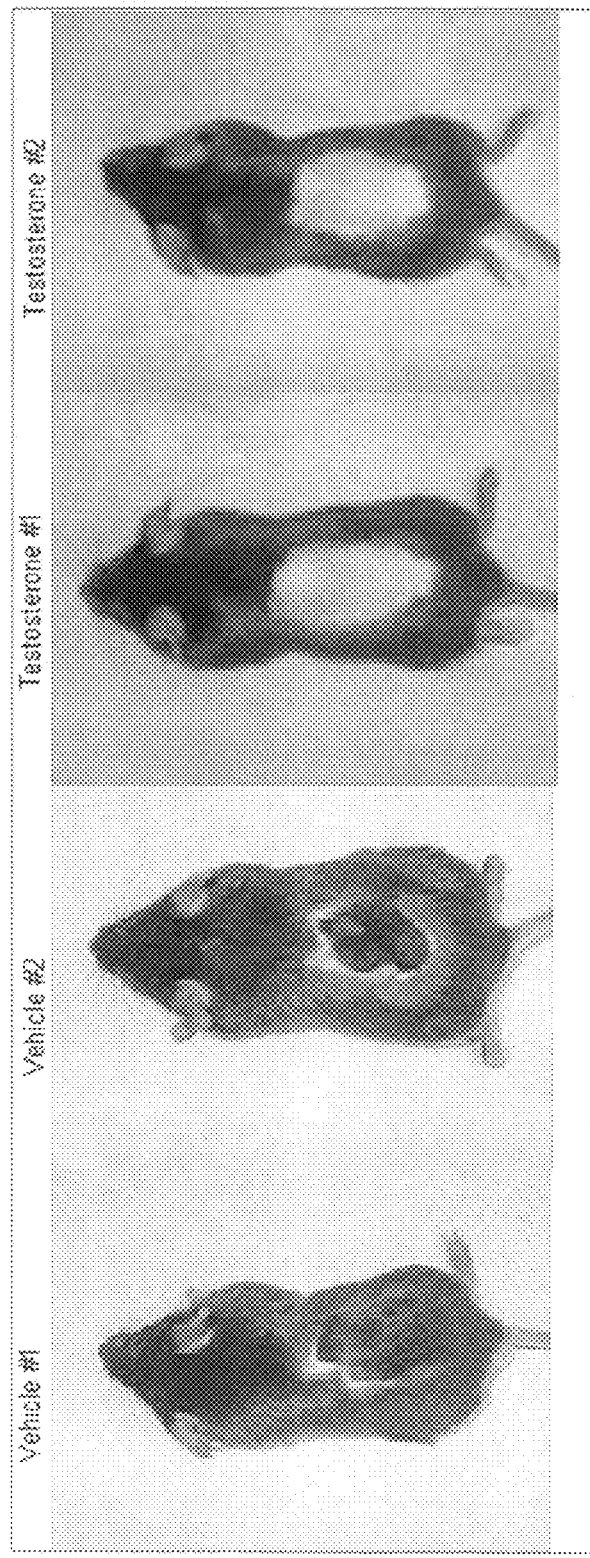
FIG. 11A depicts results from studies of an animal model of alopecia (hair loss or baldness), as described in detail in EXAMPLE 7. Six-week-old male C57BL/6J mice were shaved with an electric clipper, and then treated with a hair-removal cream. One group of mice, represented by the two left-most animals (marked "vehicle #1" and "vehicle #2") were shaved and treated only with ethanol. A second group of mice, represented by the two right-most animals (marked "testosterone #1" and "testosterone #2") were shaved and treated with a testosterone/ethanol solution in the morning and a control solution in the afternoon. The animals were photographed at the end of the 20-day treatment period. Mice treated with the ethanol vehicle alone (without testosterone) showed rapid re-growth of hair in the shaved areas after 20 days of topical treatment. Mice treated with testosterone showed little or no re-growth of hair in the shaved areas after 20 days of topical treatment.

Mice that were shaved and then received topical morning applications of testosterone and afternoon applications of the control solution only showed little or no re-growth of hair in the shaved areas after 20 days of treatment (FIG. 11A). Mice that were shaved and then received topical application of the ethanol vehicle alone (without testosterone) showed rapid re-growth of hair in the shaved areas after 20 days of topical vehicle treatment (FIG. 11A).

Figure 11B:
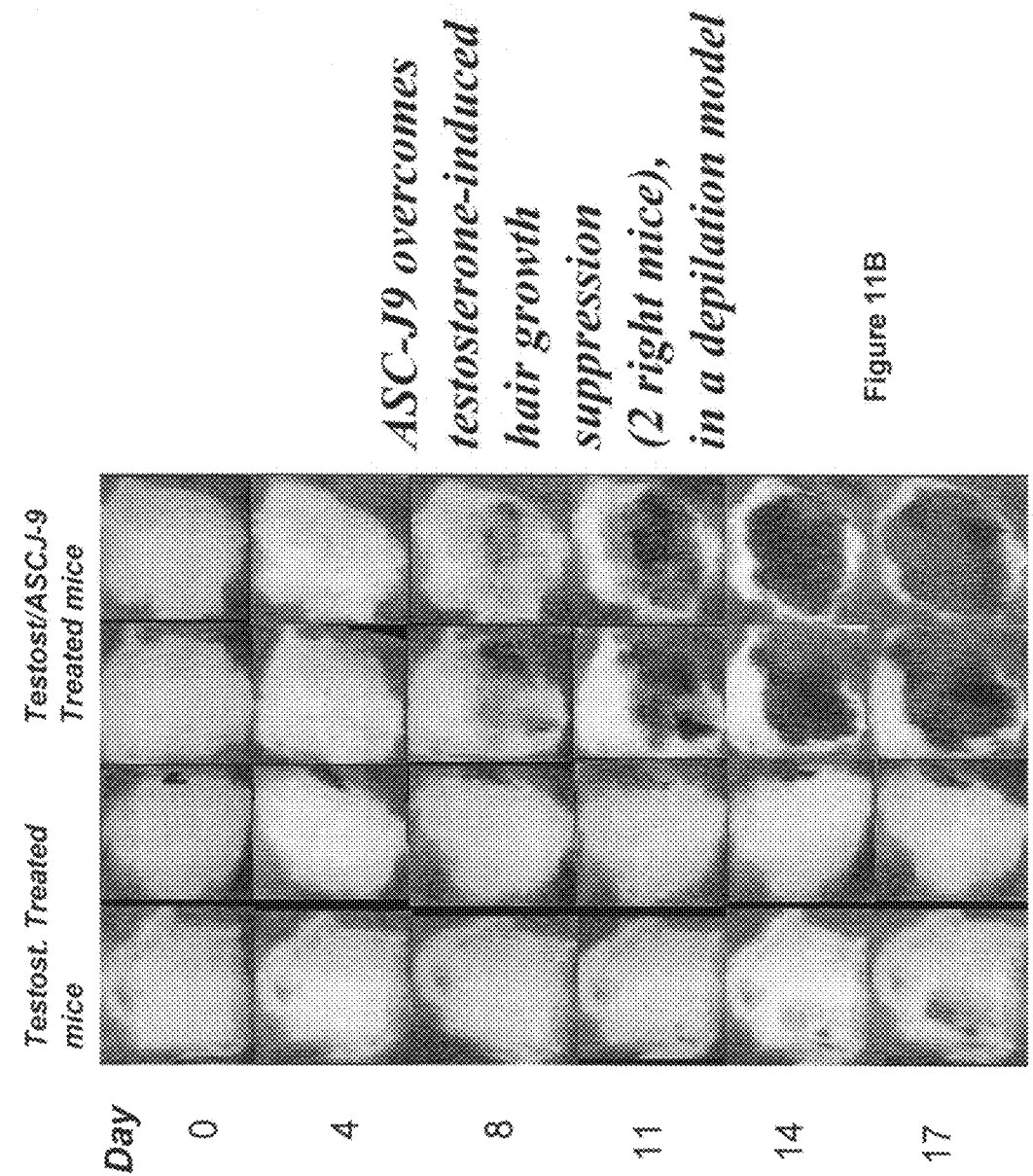
FIG. 11B depicts further results from studies of an animal model of alopecia (hair loss or baldness), as described in detail in EXAMPLE 7. Six-week-old male C57BL/6J mice were shaved with an electric clipper, and then treated with a hair-removal cream. One group of mice, (represented by the animals marked "testosterone #1" and "testosterone #2") were shaved and treated topically with testosterone in the morning and control solution in the afternoon for twenty days. A second group of mice (represented by the animals marked "ASC-J9/testosterone #1" and "ASC-J9/testosterone #2") were shaved and treated topically with testosterone in the morning and ASC-J9 in the afternoon for twenty days. Mice that received topical morning applications of testosterone and afternoon applications of the control solution only showed little or no re-growth of hair in the shaved areas after 20 days of treatment. Mice that received topical morning applications of testosterone and afternoon applications of ASC-J9 showed hair growth on day 8 and fully re-growth of hair in the shaved areas after 20 days of topical ASC-J9 treatment. These results demonstrate that topical application of ASC-J9, is able to overcome testosterone-induced hair growth suppression in an animal model.

Mice that were shaved and then received topical morning applications of testosterone and afternoon applications of the control solution only showed little or no re-growth of hair in the shaved areas after 17 days of treatment (FIG. 11B). Mice that were shaved and then received topical morning applications of testosterone and afternoon applications of ASC-J9 showed rapid re-growth of hair in the shaved areas from day 8 to day 17 (FIG. 11B). These results demonstrate that topical application of ASC-J9, a compound known to degrade the androgen receptor, is able to overcome testosterone-induced hair growth suppression in an animal model.

Example 8

In Vivo Reduction of Cancerous Tumor Using Nuclear Receptor Degradation Compound ASC-J9

Two million LNCaP tumor cells were inoculated, subcutaneously, into the left flank of nude mice. In the experimental animals, the nude mice were give an intraperitoneal (ip) injection of compound ASC-J9 at 100 mg/kg/day three times per week or with vehicle control only. After 7 weeks of treatment the tumors were excised, weighed and compared. The tumor weight in ratio of vehicle control to ASC-J9 was 0.694 g: 0.172 g therefore the ASC-J9 treated animal demonstrated a 75% reduction in tumor size. In addition, PSA (prostate specific antigen) level in plasma from animal treated with ASC-J9 reduced 90% (reduce from 57.0 ng/ml to 7.6 ng/ml). Results are shown in FIG. 12.

Example 9

Figure 13:
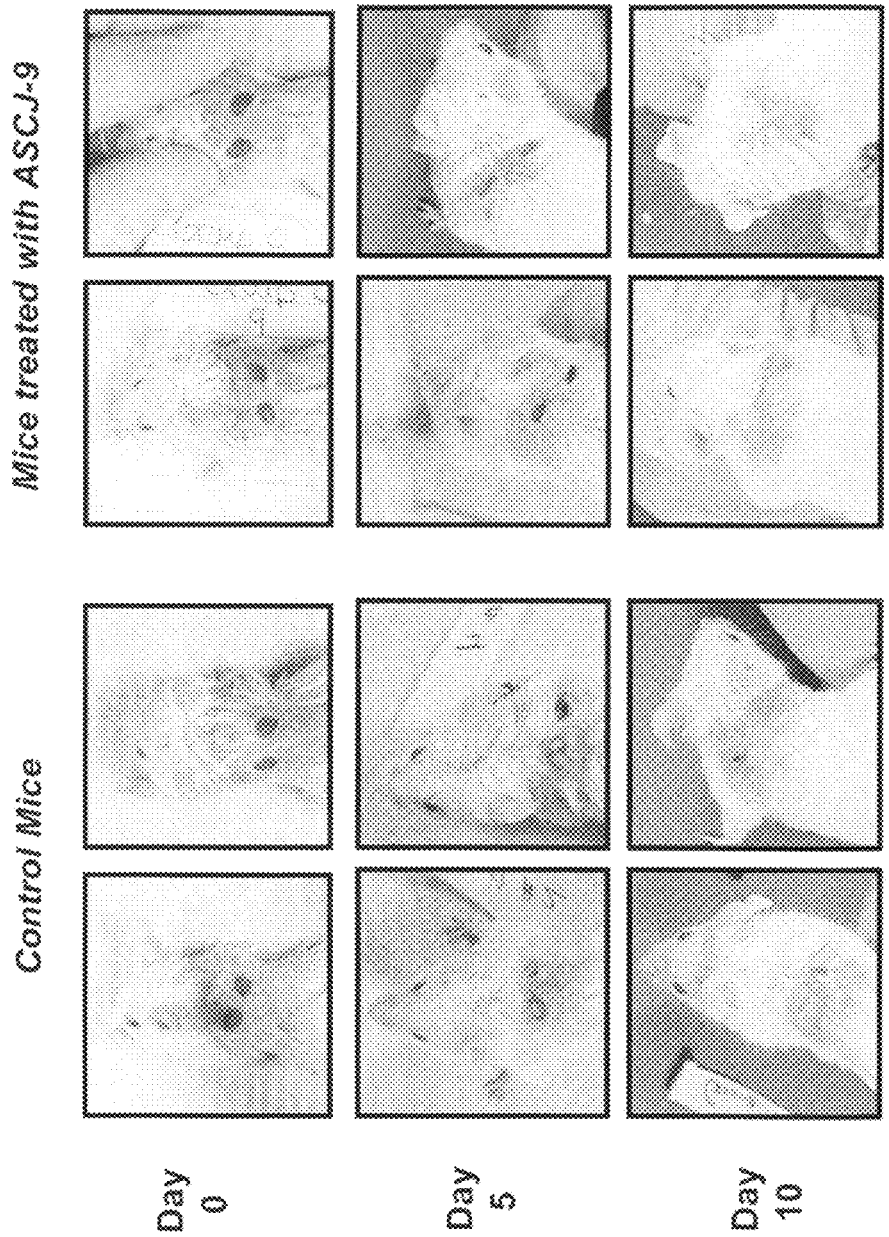
FIG. 13 demonstrates the ability of ASC-J9 to hasten wound healing in an animal model using Balb/c mice. Data depicts the results of treating artificial wounds on animal skin. Artificial skin wounds were created using a skin puncher on the neck area of retired breeder male Balb/c mice. Animals were then treated with vehicle cream or cream with ASC-J9 (25 µM) twice per day at the wound areas. Data in FIG. 13 show ASC-J9 treated animals have smaller wound openings at day 5, as compare to vehicle treated animals; and wounds were completely healed in ASC-J9 treated mice on day 10; whereas in vehicle treated animals, wound scarring remained visible. This data indicates that an ARD enhancer, ASC-J9, is capable of hastening wound healing.

ARD Enhancer ASC-J9 Compound is Capable of Hastening Skin Wound Healing in Animal Model The ability of ASC-J9 to hasten wound healing in an animal model was tested using Balb/c mice. Using a skin puncher, wounds were created near the back of the neck region on retired male breeder Balb/c mice. Mice were treated with either an ASC-J9 cream (25 uM) or a vehicle control cream twice per day topically at the wound site. Referring to FIG. 13, ASC-J9 treated animals have smaller wound size at day 5, as compare to vehicle treated animals; and wounds were completely healed in ASC-J9 treated mice on day 10 whereas vehicle treated animals wound scaring remained visible.

Example 10

Treatment of an Androgen-Related Disorder in Human Subjects by Degradation of the Androgen Receptor This example describes the treatment of a nuclear receptor-related disorder (acne vulgaris) in a subject by degradation of the nuclear receptor (the androgen receptor). Acne vulgaris, commonly known simply as acne, is a red skin rash that typically affects the face, chest, and back of teenaged and young adult humans of either sex, though it can occur at any age and on other body areas (see, for example, J. C. Harper and J. Fulton, Jr. (2003), "Acne Vulgaris", electronically available at www.emedicine.com/derm/topic2.htm, accessed 23 Apr. 2004). Acne affects nearly all people at some point in their life, and can cause permanent scarring and emotional distress and low self-esteem, as well as potentially leading to more severe health problems, such as skin infections. The androgen receptor, which is expressed in the basal cells and glandular cells of sebaceous glands, has a skin distribution that is similar between males and females (Blauer et al. (1991) *J. Investig. Dermatol.*, 97:264-268). In the skin, the androgen receptor stimulates terminal sebocyte differentiation and the production of sebum. Common treatments for acne often have undesirable side effects. For example, topical retinoids can lead to sun sensitivity, antibiotics may result in antibiotic resistance, and benzoyl peroxide can cause contact dermatitis. There is a need for novel and effective, preferably topical (non-systemic), treatments for acne.

In this example, human subjects were successfully treated for acne by topical administration of a cream containing the compound ASC-J15 or ASC-J9, which were shown in the previous examples to ameliorate the effects of the androgen receptor-activated pathway, specifically by inducing degradation of the androgen receptor. A basic carrier formulation was prepared by mixing two solutions: (1) a water-based solution containing aristoflex avc, Osmocide, Tween 20, and water; and (2) an oil-based solution containing isopropyl myristate, coconut dienthanolamine, ethylparaben, isobutylparaben, methylparaben, and propylparaben. The test compounds (ASC-J15 or ASC-J9) were added to the cream to a final concentration of 1 to 2.5 micromolar, as needed.

Figure 14A:
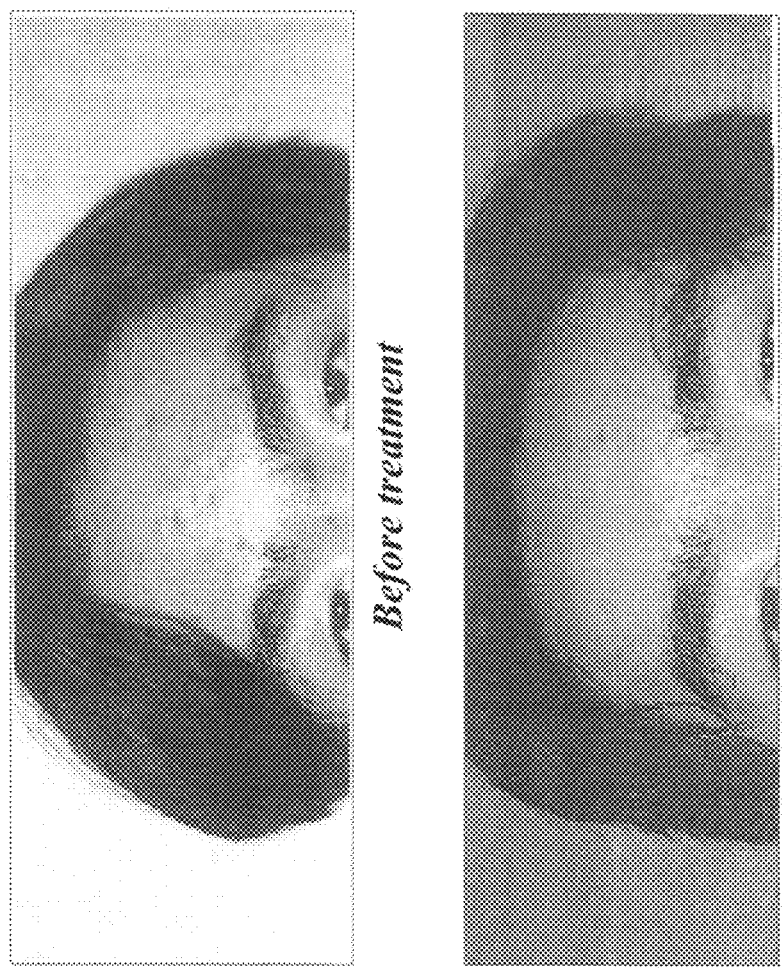
FIG. 14A depicts photographs demonstrating a representative visible improvement to skin condition resulting from topical application of the test compound ASC-J9 (2.5 micromolar in a carrier base) to the forehead of an acne-affected male volunteer and in another acne-affected male (back is shown in FIG. 14B) with ASC-J9 (625 µM), as described in detail in Example 10.
Figure 14B:
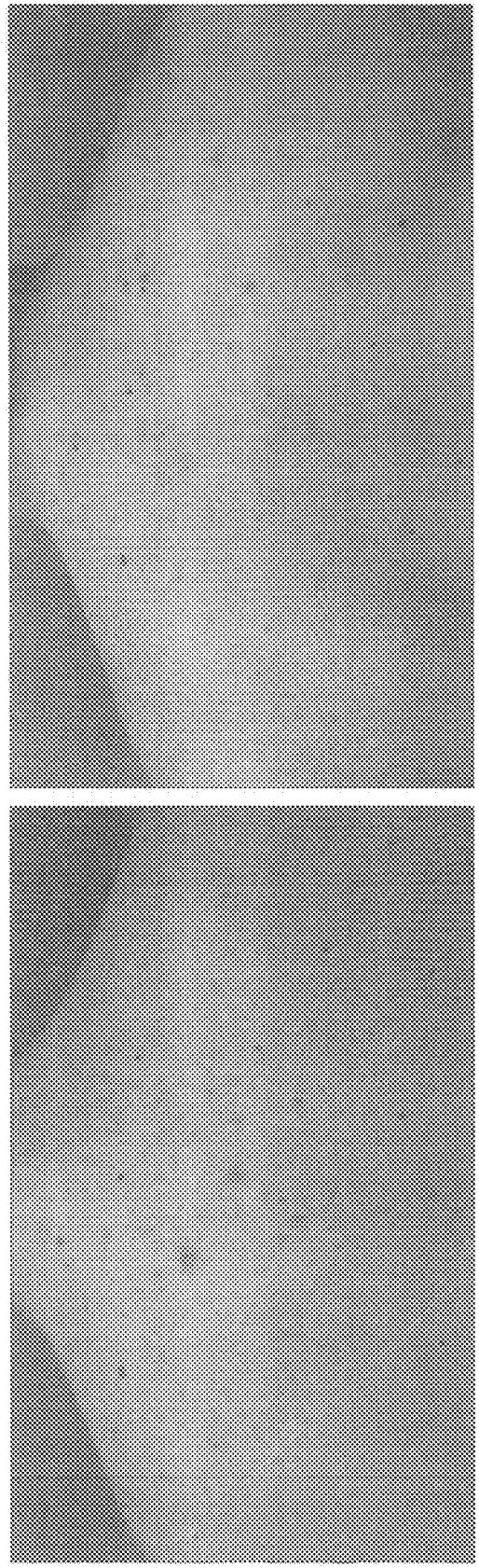

Male and female human volunteers ranging in age from 15 years to 52 years were treated by topical application of the test compounds to the acne-affected skin. Subjects were asked to apply the cream to the acne-affected areas twice a day (once in the morning and once in the evening). Generally, acne symptoms were observed to significantly subside within 2 to 3 days and completely healed within 1 to 2 weeks. The results are given in Table 2, and a representative result (photo pictures) from one volunteer is depicted in FIG. 14. FIG. 14A depicts the volunteer's forehead and FIG. 14B depicts the volunteer's back.

TABLE 2

| Subject | | | Treatment | | Relative effectiveness | Recovery Time |
|---|---|---|---|---|---|---|
| Age | Sex | Compound | Concentration (micromolar) | Frequency | | |
| 17 | F | ASCJ15 | 1 | Twice a day | ++ | 1 week |
| 15 | M | ASCJ15 | 1 | As often as needed | +++ | 1 week |
| 15 | M | ASCJ15 | 1 | As often as needed | +++ | 1 week |
| 38 | F | ASCJ15 | 1 | As often as needed | ++ | 2 weeks |
| 52 | F | ASCJ15 | 1 | Twice a day | ++ | 2 weeks |
| 42 | F | ASCJ15 | 1 | Twice a day | ++ | 2 weeks |
| 19 | M | ASCJ9 | 1 | Twice a day | + | 2 weeks |
| 18 | F | ASCJ9 | 1 | Four times a day | +++ | 1 week |
| 24 | F | ASCJ9 | 2.5 | Twice a day | +++ | 1 week |

All headings are for the convenience of the reader and should not be used to limit the meaning of the text that follows the heading, unless so specified. Various changes and departures may be made to the present invention without departing from the spirit and scope thereof. Accordingly, it is not intended that the invention be limited to that specifically described in the specification or as illustrated in the drawings, but only as set forth in the claims.

What is claimed is:

1. A pharmaceutical composition for the treatment of a skin disorder comprising:
    a) a first compound comprising androgen receptor degradation enhancer ASC-J9 and a pharmaceutically acceptable carrier, provided in a topical formulation; and
    b) a second compound comprising a retinoid and a pharmaceutically acceptable carrier, provided in an injectable formulation;
    wherein said pharmaceutical composition is provided to treat a skin disorder comprising acne.

2. The pharmaceutical composition of claim 1, wherein said skin disorder is acne.

3. The pharmaceutic composition of claim 1, wherein said first compound and said second compound are provided together.

4. The pharmaceutic composition of claim 1, wherein said first compound and said second compound are provided separately.

* * * * *